(12) United States Patent
Zobel et al.

(10) Patent No.: US 7,597,520 B2
(45) Date of Patent: *Oct. 6, 2009

(54) APPARATUS AND METHOD FOR TRANSFERRING SAMPLES FROM A SOURCE TO A TARGET

(75) Inventors: Hans-Jörg Zobel, New York, NY (US); Gerard William Leeman, Stoneham, MA (US); Amir Porat, Gany-Yehuda (IL); Moshe Gombinsky, Bat-Yam (IL)

(73) Assignee: Festo Corporation, Hauppauge, NY (US)

( * ) Notice: Subject to any disclaimer, the term of this patent is extended or adjusted under 35 U.S.C. 154(b) by 584 days.

This patent is subject to a terminal disclaimer.

(21) Appl. No.: 11/311,558

(22) Filed: Dec. 19, 2005

(65) Prior Publication Data

US 2006/0266130 A1 Nov. 30, 2006

Related U.S. Application Data

(63) Continuation-in-part of application No. 11/135,962, filed on May 24, 2005, now Pat. No. 7,534,081.

(51) Int. Cl.
*G01N 37/497* (2006.01)
(52) U.S. Cl. .................... 414/222.01; 210/695
(58) Field of Classification Search .................. 414/403, 414/785, 222.01; 210/222, 695, 416.1
See application file for complete search history.

(56) References Cited

U.S. PATENT DOCUMENTS

| | | | | |
|---|---|---|---|---|
| 2,693,979 A | * | 11/1954 | Russell | 294/65.5 |
| 4,292,920 A | | 10/1981 | Smith et al. | |
| 4,649,116 A | * | 3/1987 | Daty et al. | 435/287.2 |
| 5,055,263 A | * | 10/1991 | Meltzer | 422/65 |
| 5,288,468 A | | 2/1994 | Church et al. | |
| 5,647,994 A | * | 7/1997 | Tuunanen et al. | 210/695 |
| 5,779,907 A | | 7/1998 | Yu | |
| 6,024,925 A | * | 2/2000 | Little et al. | 422/100 |
| 6,040,192 A | | 3/2000 | Tuunanen | |
| 6,297,062 B1 | | 10/2001 | Gombinski | |

(Continued)

FOREIGN PATENT DOCUMENTS

WO   WO 87/05536   9/1987

(Continued)

*Primary Examiner*—Charles A Fox
(74) *Attorney, Agent, or Firm*—Hoffman & Baron, LLP

(57) ABSTRACT

A transfer unit for transferring a sample from a source vessel to a target vessel. The transfer unit includes a transfer device having a pin tip with a central bore terminating at a bottom wall, an actuating element movably disposed in the pin tip bore, an actuator rod for moving the actuating element and a compensating device connected between the actuating element and the actuator rod. The actuator rod moves the actuating element between a first position adjacent the tip bottom wall and a second position away from the bottom wall. Movement of the actuating element causes a sample in proximity to the pin tip to be alternately collected and released from the pin tip. Such movement also defines a stroke length for the actuator rod, wherein the compensating device compensates for any variations in the actuator rod stroke length. The transfer unit further includes a tip ejector for removing the disposable tips from the transfer device and a tip loading station for applying the tips to the transfer device.

21 Claims, 31 Drawing Sheets

U.S. PATENT DOCUMENTS

| | | |
|---|---|---|
| 6,403,038 B1 * | 6/2002 | Heermann .................. 422/101 |
| 6,409,925 B1 | 6/2002 | Gombinsky et al. |
| 6,780,648 B1 | 8/2004 | Sun |
| 2001/0055545 A1 | 12/2001 | Takii et al. |
| 2005/0035143 A1 | 2/2005 | Massaro et al. |
| 2005/0132822 A1 | 6/2005 | Massaro |

FOREIGN PATENT DOCUMENTS

| | | |
|---|---|---|
| WO | WO 94/18565 | 8/1994 |
| WO | WO 95/00247 | 1/1995 |
| WO | WO 96/09550 | 3/1996 |
| WO | WO 96/12959 | 5/1996 |
| WO | WO 99/40444 | 8/1999 |
| WO | WO 99/42832 | 8/1999 |
| WO | WO 02/49761 | 6/2002 |
| WO | WO 03/085407 A1 | 10/2003 |
| WO | WO 03/090897 A1 | 11/2003 |
| WO | WO 2004/009238 A1 | 1/2004 |
| WO | WO 2004/009300 A1 | 1/2004 |
| WO | WO 2004/035217 | 4/2004 |
| WO | WO 2004/069413 A1 | 8/2004 |
| WO | WO 2005/065831 | 7/2005 |

* cited by examiner

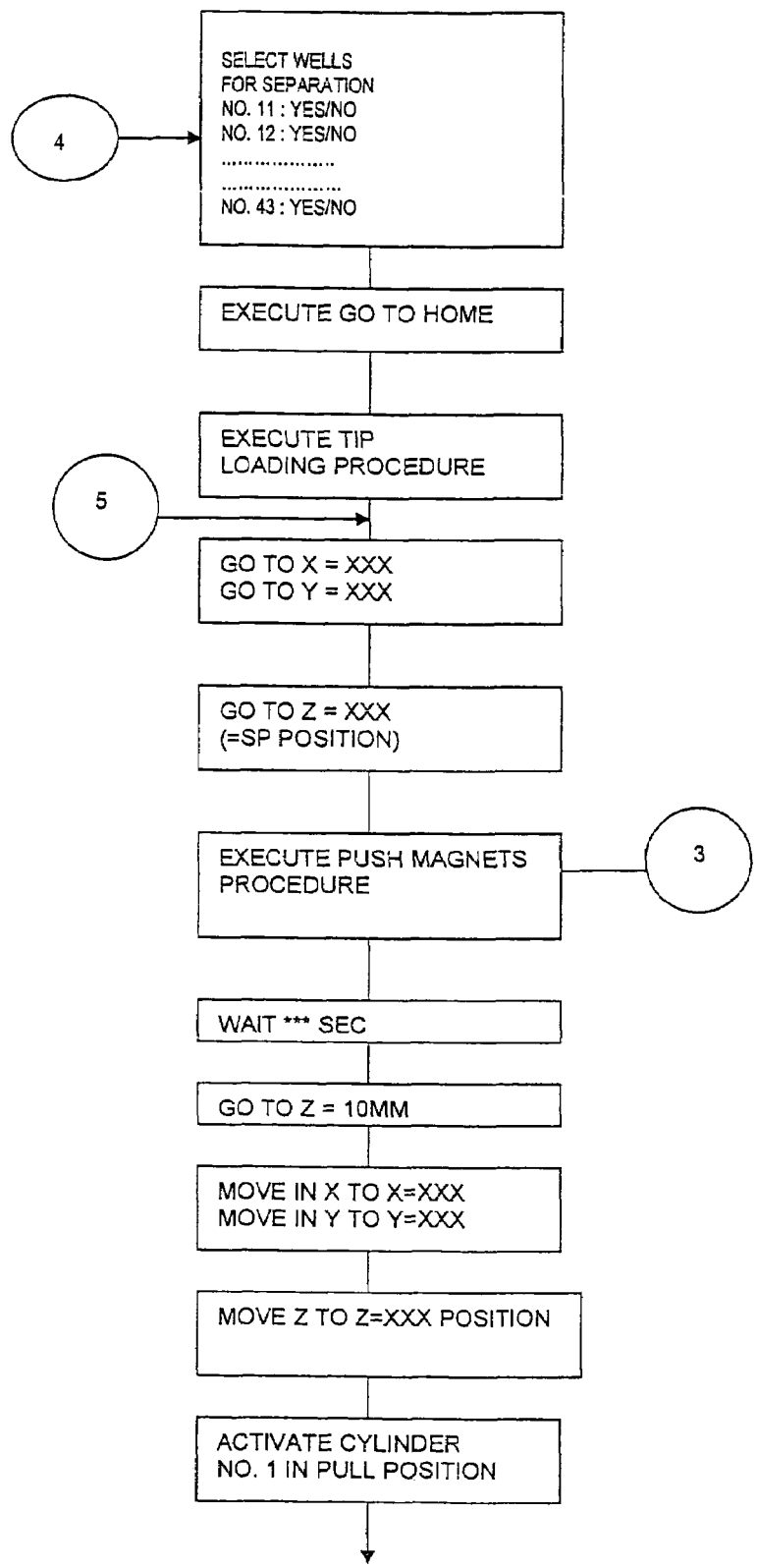
FIG. 12a  MAGNETIC SEPARATION PROCEDURE
SEE FIG. 12b

SEE FIG. 16b

SEE FIG. 17b

SEE FIG. 18b

APPARATUS AND METHOD FOR TRANSFERRING SAMPLES FROM A SOURCE TO A TARGET

CROSS-REFERENCE TO RELATED U.S. APPLICATIONS

This application is a continuation-in-part of U.S. application Ser. No. 11/135,962, filed on May 24, 2005 now U.S. Pat. No. 7,534,081.

FIELD OF THE INVENTION

The present invention relates generally to the field of analytical separation and combining of samples and, more particularly, to a system and apparatus for individually actuating and controlling a multiple array of collection members for transferring samples from a plurality of source vessels to a plurality of target vessels.

BACKGROUND OF THE INVENTION

Analytic and diagnostic procedures in the laboratory often require the transfer of a plurality of samples, simultaneously, from one array of liquid-containing wells to another. In order to transfer, add, collect or combine liquids, various multi-transferring systems have been devised. The most commonly used is a multi-pipette which collects liquid from an array of source wells for transfer to an array of target wells, simultaneously, by application or release of application, respectively, of vacuum force. In operation, the pipette for collecting or releasing of liquid is connected to a single vacuum source provided to all the pipettes in the system so that all samples in the array of wells are collected and released at once.

In recent years, magnetic particles have been used for a variety of separation, purification, and isolation techniques in connection with chemical or biological molecules. In those techniques, a molecule is coupled to a magnetic particle capable of forming a specific binding (hereinafter "affinity binding") with a molecule in a biological sample, which is to be isolated, purified or separated. The biological sample is then brought into contact with the magnetic particle and those biological molecules which bind to the magnetic particles are then isolated by application of a magnetic field.

Various devices have been developed to utilize such magnetic separation techniques in order to transfer the magnetic particles from one location to another. Indeed, magnetic separation technology has passed through several phases in the recent years. The first generation of magnetic separation technology used a two step separation technique involving a separation stand including a magnetic plate placed directly under a micro-plate. These thirty year old simple magnetic plates were composed of permanent magnets encapsulated in plastic which would contact the micro-plate vessels containing the magnetic particle suspensions. The magnetic particles within the suspensions would be drawn to the bottom or the inner surfaces of the wells in the micro-plate and the liquid was drawn out of the well or vessel leaving the magnetic particles behind. In general, such devices are termed "first generation magnetic separators."

One drawback of the "first generation" separators relates to the fact that the stationary permanent magnets positioned below the micro-plates do not come into direct contact with the magnetic particles due to the thickness of the plate and vessel sides. As a result, the magnetic field applied to the individual micro-plate wells is relatively weak due to the distance between the magnetic plate and the magnetic particles and separation is, therefore, somewhat inefficient.

To overcome this drawback, the recent second generation of magnetic separators generally employ a magnetic pipette in a one step separation process, wherein a magnetic rod is inserted into the magnetic solution to capture magnetic particles. Here, magnetic particles are attracted by strong magnetic fields to the rods and then moved out of the magnetic suspension and transferred to another vessel containing fresh washing liquid or reagent solution. The rod is then demagnetized to permit detachment of the magnetic particles into the other liquid.

Such a "second generation magnetic separator" is disclosed, for example, in U.S. Pat. No. 4,292,920. This device includes a single or multi-pin arrangement, corresponding to a micro-well arrangement, which is capable of insertion into the wells of a micro-plate to attract magnetic particles by magnetic force. In one embodiment, the pin is connected to an electromagnet, and by turning the electromagnet on and off the pin becomes magnetized, or non-magnetized, respectively.

Another "second generation magnetic separator" is disclosed in U.S. Pat. No. 5,567,326, which shows an apparatus and method for separating magnetically responsive particles from a nonmagnetic test medium in which they are suspended. The device comprises a plurality of nonmagnetic pins (termed "magnetic field directing elements") arranged in an array, and a magnet positioned normal to the array. Placing the magnet on the array of pins renders all the pins in the array magnetic thereby causing particles to be attracted to them. Removing the magnet causes the pins to become non-magnetic, and consequently the magnetic particles are released from the pins.

The drawbacks of the above "second generation separators" reside in the fact that the magnetic rods or pins come into direct contact with the magnetic particles, so that if rinsing and sterilization is required, the whole apparatus or device has to be washed. Such a procedure is expensive and time consuming. Furthermore, even where the magnetic rods are covered with disposable protective tips, the collection of particles is not efficient since some of the particles remain in the suspension due to surface tension forces. Another drawback of these devices reside in the fact that where a multi-pin device is used to collect magnetic particles from a plurality of wells, all of the pins are fixed to a movable head and travel up and down as a unit such that all of the samples from all the wells have to be collected at once in an "all or none" fashion. Thus, it is not possible to selectively collect particles from only selected wells in an array.

In U.S. Pat. No. 6,409,925, Gombinsky et al. disclose a "third generation magnetic separator." The '925 patent discloses a device wherein each collecting pin can be independently controlled. Specifically, the disclosed magnetic rod design allows for a magnet disposed therein to be freely and independently movable up or down to thereby magnetically energize and de-energize the rod. Thus, each rod is independently magnetized regardless of the magnetization of the other rods. This unique feature permits multiple degrees of freedom (i.e., pin head movement and independent magnet movement) compared to "second generation" systems that have only one degree of freedom.

Accordingly, it would be desirable to improve upon the latest "third generation" magnetic separator technology in various ways to provide a complete control and actuation system that utilizes third generation technology. It would be further desirable to provide such a system with a selectable bottom magnet array and a combinatorial tip loader for the upper pin device.

SUMMARY OF THE INVENTION

The present invention is a control system for transferring a sample from a source vessel to a target vessel. The control system generally includes a vessel unit, a primary transfer unit, an x-drive, a y-drive, a z-drive and a control unit for controlling the drives. The vessel unit includes a translatable support plate for supporting the source vessel and the target vessel thereon and the transfer unit includes at least one transfer device for transferring the sample from the source vessel to the target vessel. The x-, y- and z-drives reciprocally translate one of the support plate and the transfer device in a respective x-direction, y-direction and z-direction, wherein the x, y and z directions define a three axis Cartesian coordinate system.

The present invention may take the form of a control system wherein the primary transfer unit comprises a primary magnet unit and the transfer device uses a magnetic force to attract the sample thereto. Additionally, the vessel drive unit is further preferably in the form of a micro-well drive unit including a translatable support plate for supporting a micro-well tray having at least one of the source vessel and the target vessel thereon.

In a preferred embodiment, the primary magnet unit includes an array of pins and a magnet actuator system for selectively applying and removing the magnetic force at the tip of at least one pin of the pin array. The pin further preferably includes a hollow pin body terminating in a tip and a magnet slidably disposed within the hollow pin body, wherein the magnet actuator system drives the magnet within the hollow pin body to move from a first position adjacent the tip of the pin to a second position away from the tip. When the magnet is adjacent the tip, the magnetic force is applied at the tip and when the magnet is away from the tip, the magnetic force is removed from tip.

The magnet actuator system preferably includes an actuator plate having at least one individually activated electromagnet disposed thereon, an actuator plate drive for reciprocally translating the actuator plate and a magnet rod having a distal end connected to the magnet in the hollow pin body. The magnet rod, which may take the form of a flexible cable, includes a ferromagnetic piston portion engageable with the electromagnet when the electromagnetic is activated for moving the magnet from the first position to the second position upon translation of the actuator plate. Also, the actuator system further preferably includes a piston housing spaced from the actuator plate. The piston housing can include a tension spring connected to the ferromagnetic piston portion of the magnet rod for biasing the piston portion toward the piston housing. Preferably, the piston housing includes a permanent magnet for biasing the ferromagnetic piston toward the piston housing.

In an alternative embodiment, the magnet actuator system includes a magnet rod having a proximal end and a distal end, and an individually activated magnet rod drive. The distal end of the magnet rod is connected to the magnet in the hollow pin body and the magnet rod drive is connected to the proximal end of the magnet rod for moving the magnet from its first position to its second position.

The magnetic pin control system of the present invention further preferably includes a secondary magnet unit including at least one secondary magnet element supported on a secondary magnet plate, wherein the support plate of the micro-well drive unit is disposed between the pin tip of the primary magnet unit and the secondary magnet element of the secondary magnet unit. The secondary magnet further preferably includes its own y-axis secondary magnet plate drive for reciprocally translating the secondary magnet plate in the y-direction and a z-axis secondary magnet plate drive for reciprocally translating the secondary magnet plate in the z direction.

Like the pin, the secondary magnet element is preferably part of an array of secondary magnet elements which are adapted to be selectively activated and de-activated for alternately applying and removing a magnetic field at a bottom of the micro-well tray. This can be achieved with a secondary magnet actuator system that drives a magnet slidably disposed in a bore of the secondary magnet plate between a first position adjacent the micro-well support plate for applying the magnetic field to a respective well of the micro-well tray, to a second position away from the micro-well support plate for removing the magnetic field from the respective well of the micro-well tray. Here too, the secondary magnet actuator preferably includes an actuator plate having at least one individually activated electromagnet disposed thereon, an actuator plate drive for reciprocally translating the actuator plate and a magnet rod having a distal end connected to the magnet in the secondary magnet plate, wherein the magnet rod includes a ferromagnetic piston portion engageable with the electromagnet when the electromagnetic is activated for moving the magnet from the first position to the second position upon translation of the actuator plate.

The pin control system of the present invention may further include a tip insertion unit for applying a disposable tip to the pin of the primary magnet unit and a tip removal unit for removing the disposable tip from the pin. The tip insertion unit may include a block having a bore formed therein. The bore has a proximal end and a distal end. The proximal end is sized to receive the disposable tip for application to the pin and a pressure source is connected to the distal end of the bore for applying a pressure in the bore for forcing the disposable tip out of the bore. A piston slidably received within the bore may also be provided for forcing the disposable tip out of the bore under the influence of the pressure.

The tip removal unit may include a fork defined by at least one channel having a width corresponding to a diameter of the pin. The channel is adapted to engage the disposable tip of the pin when the pin is brought into the channel.

The present invention further involves a method for transporting a sample from a source vessel to a target vessel. The method generally includes the steps of supporting the source vessel and the target vessel on a translatable support plate, translating the support plate in an x-direction to position the source vessel below a transfer device of a primary transfer unit, translating the primary transfer unit in a y-direction to position the transfer device above the source vessel, translating the primary transfer unit in a z-direction to lower the transfer device into the source vessel, activating the transfer device to collect the sample contained in the source vessel, translating the primary transfer unit in the z-direction to raise the transfer device out of the source vessel, translating the primary transfer unit in the y-direction to position the transfer device above the target vessel, translating the support plate in the x-direction to position the target vessel below the transfer device of the primary transfer unit, translating the primary transfer unit in the z-direction to lower the transfer device into the target vessel and deactivating the transfer device to release the sample from the transfer device into the target vessel.

According to the present invention, the x, y and z directions described above define a three axis Cartesian coordinate system.

In a preferred embodiment, the primary transfer unit is in the form of a primary magnet unit and the transfer device is in the form of a pin having a tip. In this case, the activating step involves the step of applying a magnetic force at the tip to attract magnet particles of the sample contained in the source vessel and the deactivating step involves the step of removing the magnetic field from the tip to release the magnet particles from the tip into the target vessel. The magnetic force is preferably applied by moving a magnet within a hollow body of the pin to a first position adjacent the tip of the pin and the magnetic force is removed by moving the magnet to a second position away from the pin tip. Also, the step of moving the magnet to the first position preferably includes the steps of engaging a ferromagnetic piston portion of a magnet rod connected to the magnet with an electromagnet fixed on an actuator plate and translating the actuator plate. Preferably, movement of the piston is biased by a permanent magnet or a tension spring.

The method of the present invention further preferably includes the step of providing a secondary magnet unit below the translatable support plate opposite the primary transfer unit, wherein the secondary magnet unit includes at least one secondary magnet element supported on a secondary magnet plate. The secondary magnet unit may be translated in the y-direction and the z-direction to position the secondary magnet element under the transfer device of the primary transfer unit.

Additionally, the secondary magnet element may be selectively activated and de-activated for alternately applying and removing a magnetic field at a bottom of the translatable micro-well support plate. The step of selectively activating and de-activating the secondary magnet element preferably includes the step of moving a magnet disposed within a bore of the secondary magnet plate between a first position adjacent the translatable micro-well support plate and a second position away from the translatable micro-well support plate. The magnet may be moved by engaging a ferromagnetic piston portion of a magnet rod connected to the magnet with an electromagnet fixed on an actuator plate and translating the actuator plate.

Moreover, the method of the present invention may further include the steps of translating the primary magnet unit in the y-direction and the z-direction to position the pin tip adjacent a tip insertion unit and applying a disposable tip on the pin with the tip insertion unit. This can be accomplished by applying a pressure within a bore having the disposable tip seated therein, wherein the pressure forces the tip out of the bore and onto the pin.

Furthermore, the method of the present invention may further include the steps of translating the primary magnet unit in the y-direction and the z-direction to position the pin adjacent a tip removal unit and removing a disposable tip from the pin with the tip removal unit. This can be accomplished by positioning the pin within a channel of a fork of the tip removal unit and lifting the pin, wherein the disposable tip engages the fork and is removed from the pin.

Of course, the system can also be operated by selecting any pin combination within the array permitting quantitative collection of particles from a given magnetic suspension. This feature of quantitative separation and transfer allows for dividing a sample into sub-samples. Also, the present invention allows for the sample particles to be washed efficiently with a "flip-flop" movement of particles due to magnets moving under the sample wells.

The present invention further involves a system for transferring samples from a source vessel to a target vessel including a transfer device having a hollow body and an actuating element movably disposed in the hollow body between a first and a second position. Movement of the actuating element causes a sample in proximity to the transfer device to be alternately collected and released from the transfer device. The system further includes an actuator plate having at least one individually activated electromagnet disposed thereon, an actuator plate drive for reciprocally translating the actuator plate and an actuator rod having a distal end connected to the actuating element in the hollow body of the transfer device. The actuator rod includes a ferromagnetic piston portion engageable with the electromagnet when the electromagnetic is activated for moving the actuating element from the first position to the second position upon translation of the actuator plate.

In a preferred embodiment, the transfer device of the primary transfer unit includes a pin tip having a central bore terminating at a bottom wall, an actuating element movably disposed in the pin tip bore, an actuator rod for moving the actuating element and a compensating device connected between the actuating element and the actuator rod. The actuator rod moves the actuating element between a first position adjacent the tip bottom wall and a second position away from the bottom wall. Movement of the actuating element causes a sample in proximity to the pin tip to be alternately collected and released from the pin tip. Such movement also defines a stroke length for the actuator rod, wherein the compensating device compensates for any variations in the actuator rod stroke length.

Again, the actuating element is preferably a magnet for alternately applying and removing a magnetic force at the pin tip. The compensating device preferably urges the actuating element into contact with the pin tip bottom wall at the first position. In this regard, the compensating device is preferably a resilient element for biasing the actuating element against the pin tip bottom wall at the first position. More specifically, the compensating device preferably includes a tubular member having a central bore and a spring disposed within the bore. The actuating element is fixed at one end of the tubular member and the actuator rod movably extends into the central bore to engage the spring.

In an alternative embodiment, a tip ejector for removing the disposable tips from the transfer unit can be provided directly on the transfer device head assembly. In particular, the transfer unit can include a head assembly, a transfer device supported on the head assembly and a tip ejector supported on the head assembly for removing a disposable tip from the transfer device. The tip ejector preferably includes an ejector plate having an aperture defined by an edge and a drive supported on the head assembly and connected to the ejector plate for moving the ejector plate away from the head assembly. The transfer device extends through the aperture on the ejector plate and the aperture edge engages the tip to remove the tip from the transfer device upon movement of the ejector plate away from the head assembly.

In another alternative embodiment, the tip loading station can include a base having a bore formed therein, a sub-base supported on an upper surface of the base and a pressure source connected to the base. The bore in the base has a proximal end terminating at an upper surface of the base and a distal end. The sub-base supports a tip for application to the transfer device and the pressure source is connected to the distal end of the base bore for applying a pressure through the base bore for forcing the tip from the sub-base onto the transfer device.

The sub-base can be adapted to support a plurality of tips and can be translatable with respect to the base to positively position the tips over the base bore. Also, the tip loading station can further include a tip cassette supported on the sub-base. The tip cassette has a bore formed therethrough, which is sized to receive the tip and also has a distal end terminating at the upper surface of the base.

The preferred embodiments of the control system as well as other objects, features and advantages of this invention, will be apparent from the following detailed description, which is to be read in conjunction with the accompanying drawings.

BRIEF DESCRIPTION OF THE DRAWINGS

FIGS. 12a and 12b is a flow chart showing operation of the system according to the present invention.

DETAILED DESCRIPTION OF THE PREFERRED EMBODIMENTS

Figure 1:
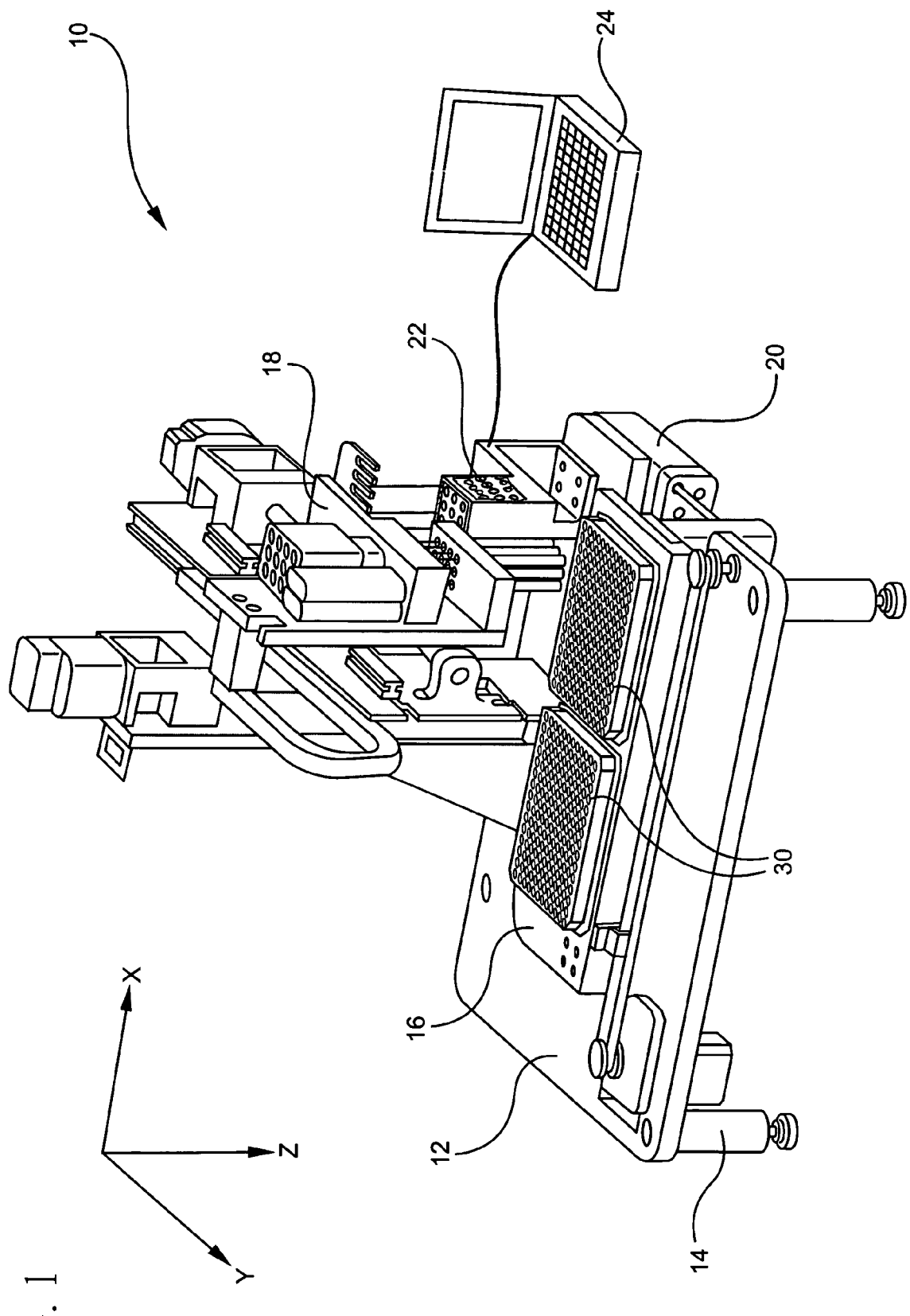
FIG. 1 is a top perspective view of the overall system formed in accordance with the present invention.

Referring first to FIG. 1, the pin control system 10 of the present invention generally includes five major functional components provided on a supporting structure or frame 12 having a plurality of legs 14 for supporting the system 10 on a surface. The major functional components of the system 10 include a vessel unit 16, a primary transfer unit 18, a secondary magnet unit 20, a tip insertion/removal station 22 and a central control unit 24.

Figure 2:
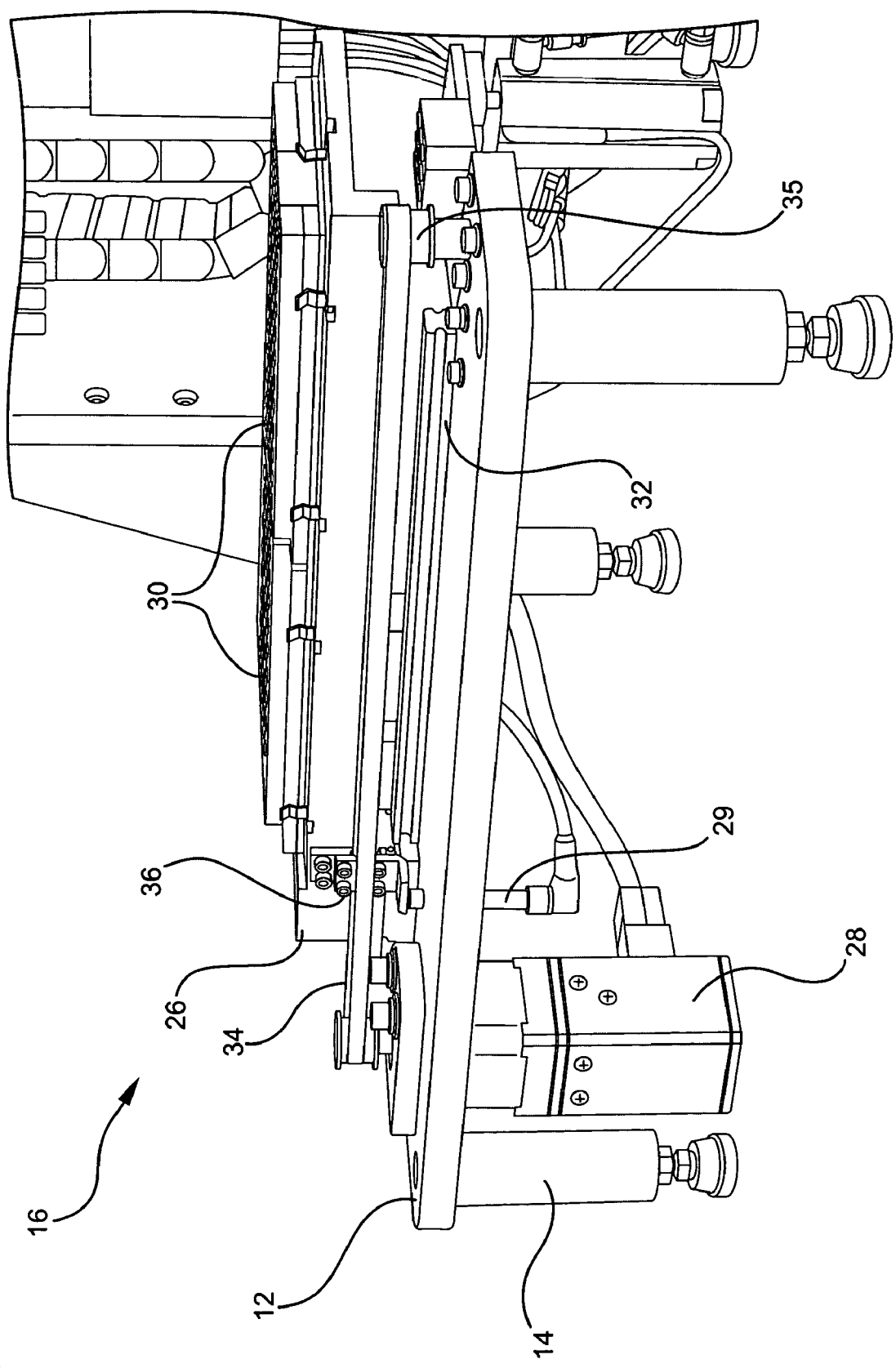
FIG. 2 is a top perspective view of the system shown in FIG. 1 with the micro-well tray drive unit shown in greater detail.

Referring additionally to FIG. 2, the vessel unit 16 preferably includes a translatable support plate 26 and a motor 28 for reciprocally translating the support plate in the x-direction with respect to the system frame 12, as shown in FIG. 1. The translatable support plate 26 supports a source vessel containing a sample to be transferred and a target vessel to which the sample is transported. It is of course conceivable for the support plate 26 to support multiple samples which can be simultaneously transported from respective source vessels to respective target vessels. In a preferred embodiment, the source and target vessels are defined in one or more micro-well trays 30 and the translatable support plate 26 is adapted to support at least one and preferably two standard size micro-well trays having a matrix of n wells. In a preferred embodiment, the matrix of wells carries a magnetic suspension for bio-analytical processes and synthesis therein. It is also conceivable that additional micro-well support plates 26 can be provided on the system frame 12 depending on the system requirements. The support plate 26 further preferably has an open frame construction so that the bottoms of the micro-well trays are accessible from below by the secondary magnet unit 20, as will be described in further detail below.

The support plate 26 is engageable with a rail 32 fixed to the system frame 12 to facilitate smooth translation back and forth in the x-direction. The micro-well motor 28 may be coupled to the plate 26 via a belt 34 and pulley 35 arrangement, whereby the plate includes a carriage 36. The micro-well motor 28 is preferably a standard compact stepper motor. A suitable stepper motor for the present invention is Festo Product No. MTRE-ST, which is a two phase hybrid stepper motor with an integrated power amplifier.

Figure 3:
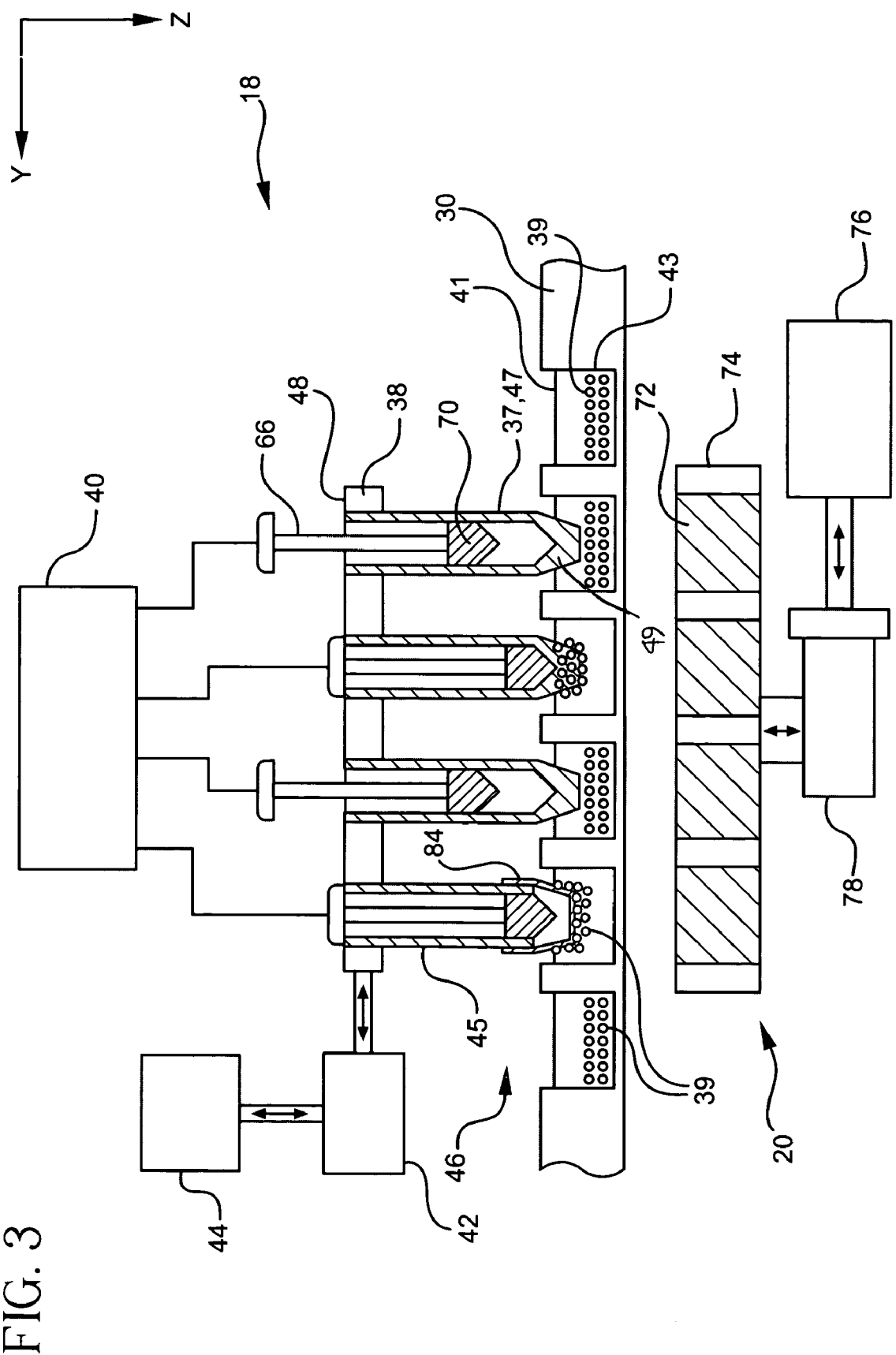
FIG. 3 is a schematic diagram of the functional components of the primary magnet unit and the secondary magnet unit.

FIG. 3 is a schematic diagram showing the functional components of the primary transfer unit 18 and the secondary magnet unit 20. The primary transfer unit 18 generally includes at least one transfer device 37 for transporting a sample from the source vessel to the target vessel. Preferably, and as will be discussed in further detail below, the primary transfer unit 18 includes a head assembly 38 supporting an array of transfer devices 37, wherein each transfer device is capable of being selectively activated to transfer samples from respective source vessels to respective target vessels.

Figure 9:
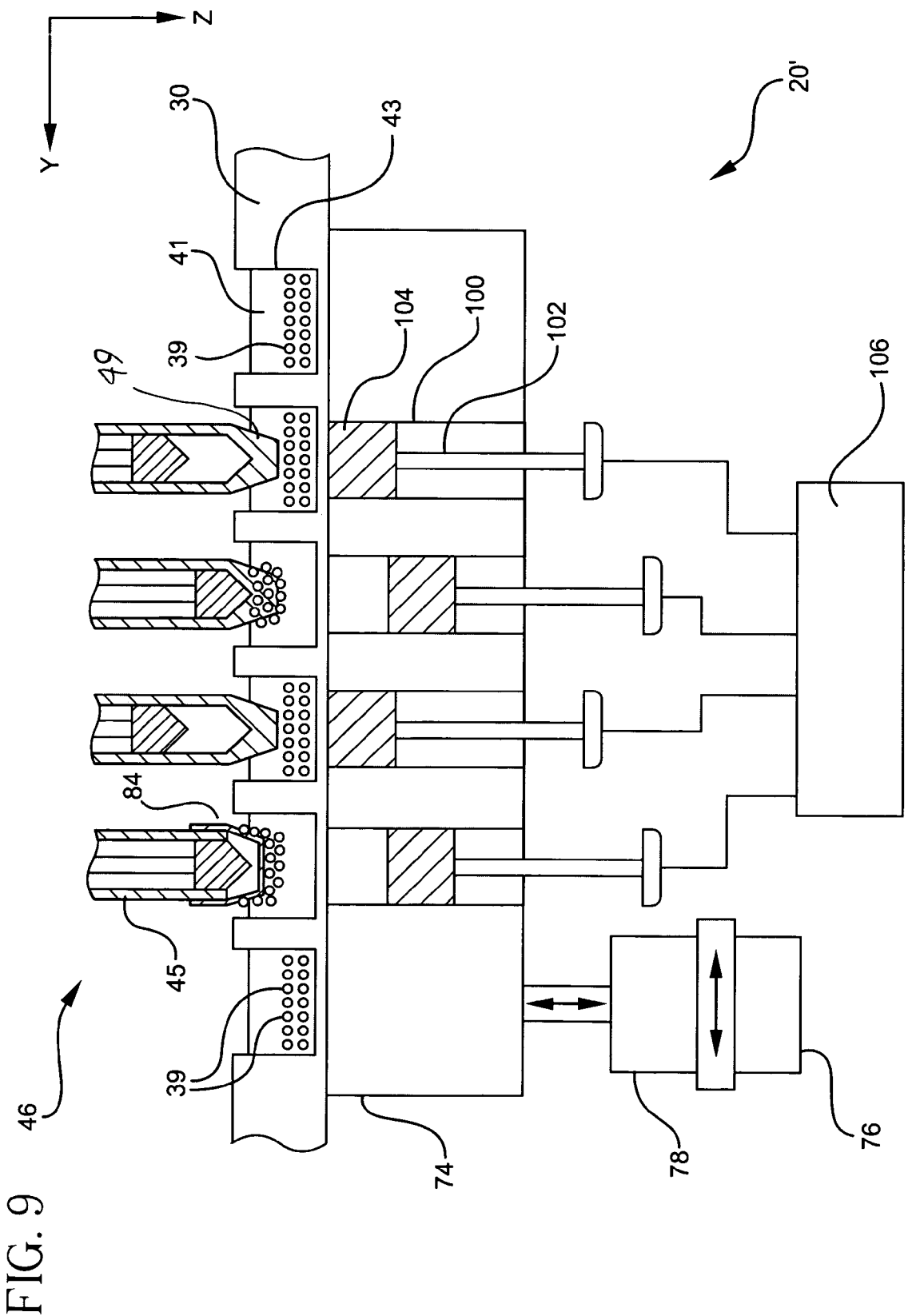
FIG. 9 is a general schematic diagram of the functional components of the preferred embodiment of the secondary magnet unit.
Figure 10:
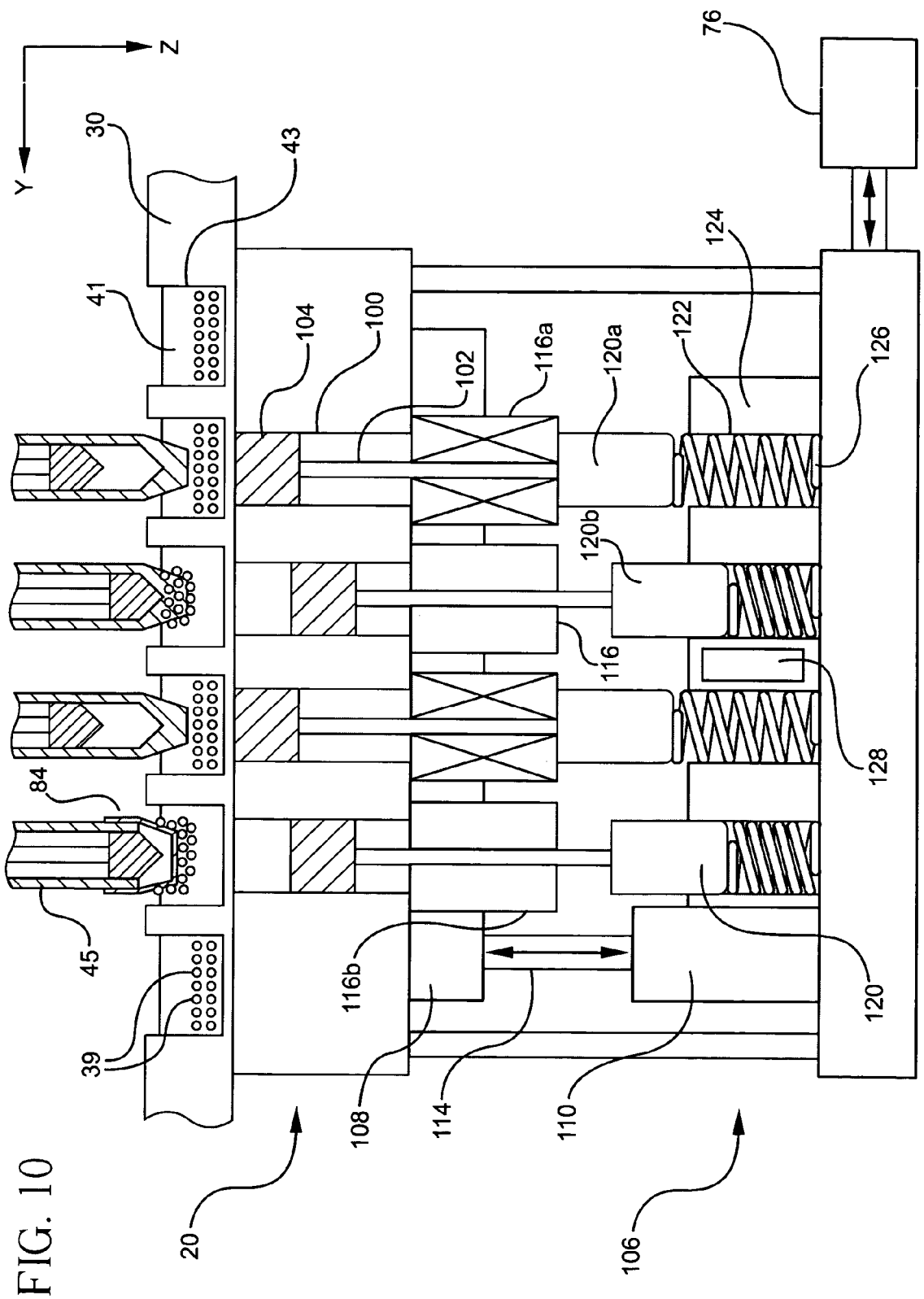
FIG. 10 is a cross-sectional view of the preferred embodiment of the secondary magnet rod actuator system of the secondary magnet unit.

In a preferred embodiment, the primary transfer unit 18 is in the form of a primary magnet unit and the transfer device 37 is in the form of an array 46 of pins 47, each having a hollow pin body 45 terminating in a tip 49. As shown in FIGS. 3, 9 and 10, the tips 49 may be integral with the hollow pin body, or, as will be discussed in further detail below, in the preferred embodiment, the tips take the form of disposable tips 84, which are separable from the body of the pins.

The primary magnet unit 18 further includes an actuator system 40, a y-axis motor 42 and a z-axis motor 44. As will be explained in further detail below, the multi-pin head assembly 38 is driven in the y and z directions by the respective motor 42 and 44 to interact with the micro-well trays 30 driven in the x-direction by the micro-well drive unit 16. Thus, a three-axis Cartesian coordinate system is established.

It is to be understood that the arrangement of the x-drive 28, y-drive 42 and z-drive 44 is described herein in an exemplary preferred embodiment. Those skilled in the art will appreciate that the three axis drives may be positioned in different arrangements, wherein, for example, the y-drive and/or the z-drive translate the support plate 26 in the y-direction and/or the z-direction. Similarly, the support plate 26 supporting the micro-well trays 30 may be stationary, whereas the transfer device 37 may be provided with three-axis movement. Such alternate drive arrangements are intended to come within the scope of the invention.

Figure 4:
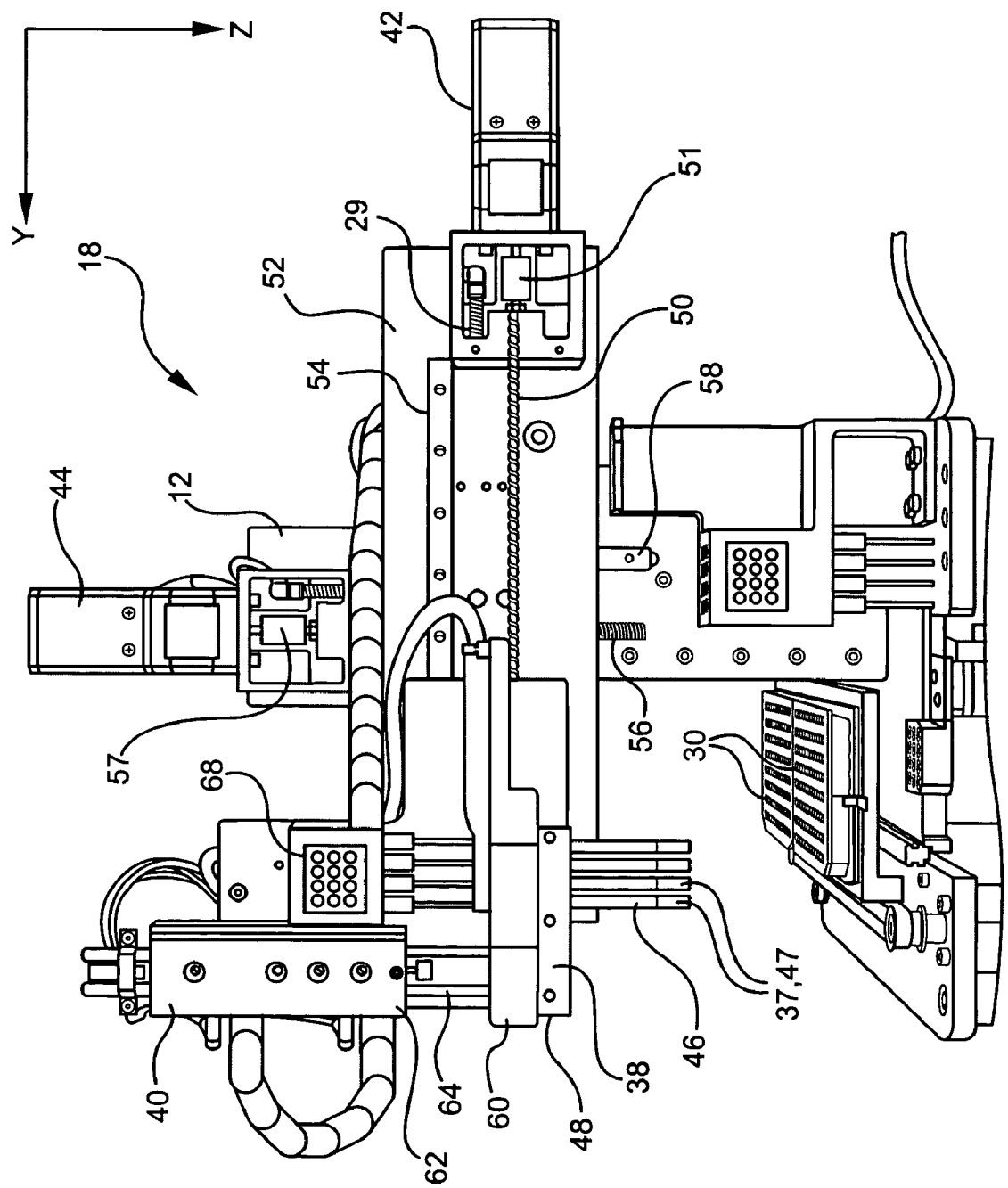
FIG. 4 is a plan view of the system shown in FIG. 1 with the primary magnet unit shown in greater detail.

Returning to the preferred embodiment shown in FIG. 4, the transfer devices 37 or pins 47 are secured to a bottom leg of an angle plate 48 in a conventional manner so that the pins 37, 47 point downward in the z-direction. The array 46 shown in the drawings is a 4×3 array of twelve devices/pins 37, 47, but other numbers or arrays of pins may be utilized. The upwardly extending leg of the angle plate 48 is coupled to the y-axis motor 42 via a ball screw 50 and actuator 51. In this manner, the angle plate 48 with the pin array 46 are translatable in the y-direction by the y-axis motor 42. The angle plate 48 and the y-axis motor 42 are in turn attached to a z-axis plate 52, which is translatable in the z-direction. The angle plate 48 is preferably supported on a rail 54 fixed to the z-axis plate 52 to permit translation of the angle plate, and thus the pin array 46, in the y-direction. Linear bearings (not shown) may be provided on the angle plate 48 to facilitate smooth translation.

The z-axis plate 52 is coupled to the z-axis motor 44 by a similar ball screw 56, actuator 57 and rail 58 arrangement. In particular, the z-axis plate 52 is preferably, translatably supported on a rail 58 fixed to the system frame 12 so that the z-axis plate, along with the pin array 46, can be driven in the z-direction by the z-axis motor with respect to the system frame.

Figure 5:
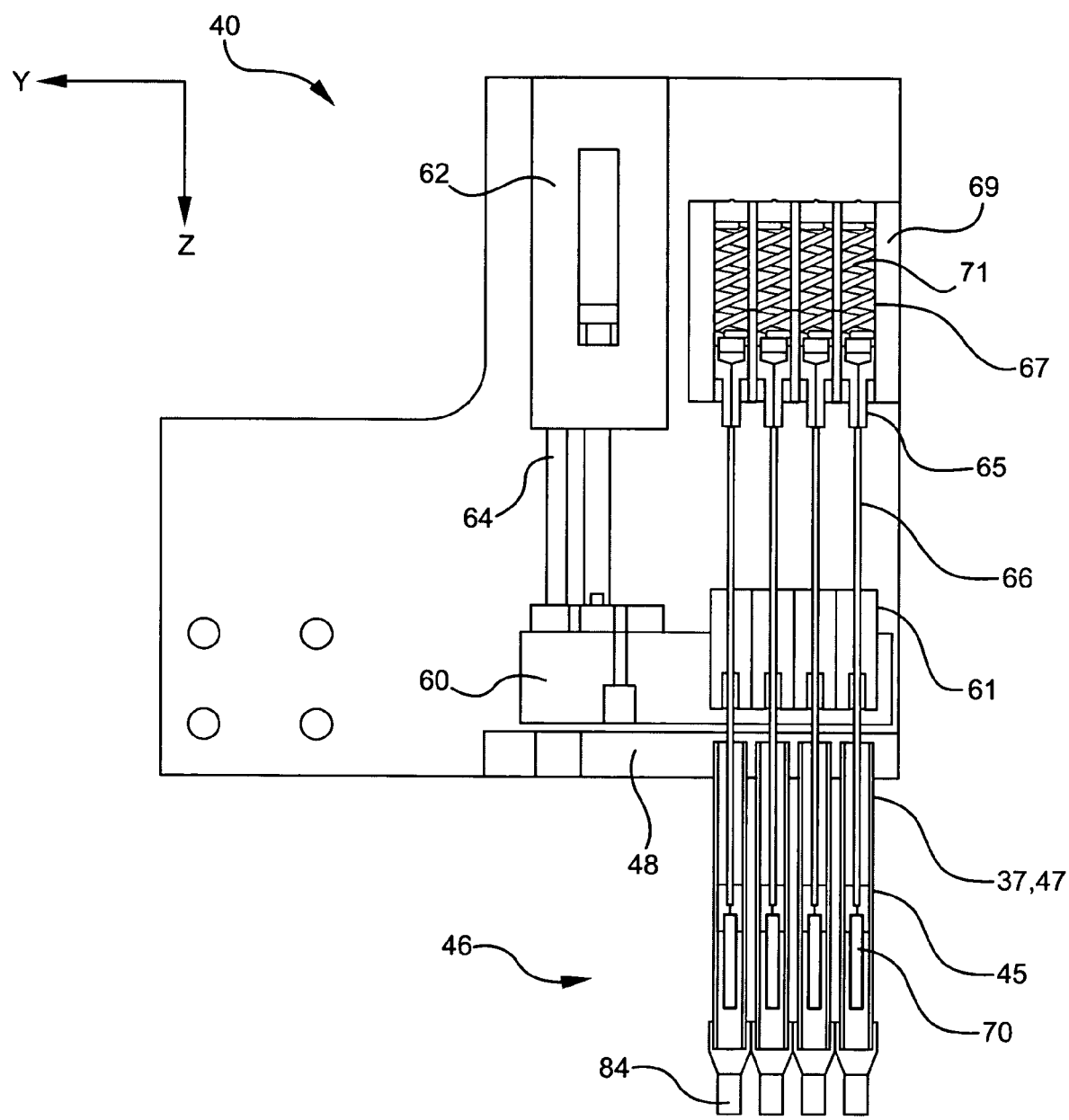
FIG. 5 is a cross-sectional view of the preferred embodiment of the magnet rod actuator system of the primary magnet unit.

Referring additionally to FIG. 5, the transfer device 37 is preferably in the form of a pin 47 having a hollow body 45 and a removable tip 84 attached at an end thereof. The pin 47 further includes an actuating element 70 movably disposed in the body 45 between a first position adjacent the tip 84 and a second position away from the tip. This movement of the actuating element 70 causes a sample in proximity to the tip 84 of the transfer device 37 to be alternately collected and released from the tip of the transfer device.

In a preferred embodiment, the actuating element 70 is a magnet which applies a magnetic force at the tip 49, 84 of the pin 47 when it is positioned adjacent the tip to attract magnetic particles 39 suspended in the liquids 41 contained in the wells 43 of the micro-well tray 30, as shown in FIG. 3. When the magnet 70 is retracted or withdrawn away from the tip 49, 84 of the pin 47, the magnetic force is thereby removed and the magnetic particles 39 are released from the tip. This interaction between the magnet rods 66 and the pins 47 and the resulting magnetic operation of the pin array 46 is further described in U.S. Pat. No. 6,409,925 to Gombinsky et al., the disclosure of which is incorporated herein by reference.

In an alternative embodiment, the actuating element may take the form of a piston or a plunger which alternately creates a positive pressure or a suction within the hollow body 45. Such positive pressure may be used to discharge a sample 41 from an opening at the tip of the transfer device. Conversely, such suction may be used to draw in a sample through an opening of the tip. This operation is similar to that of a conventional syringe, pipette, or other known device for supplying and/or releasing a vacuum.

In either embodiment, individual movement of the actuating elements 70 with respect to the pins 37, 47 is controlled by the actuator 40. Such "combinatorial" movement can be achieved pneumatically, wherein each pin 37,47 is connected to air lines for the supplying and release of pneumatic forces to move the actuating elements 70 as desired. Alternatively, solenoid valve-equipped pipettes, instead of magnets can also be used with the present invention for the transportation of beads. However, in a preferred embodiment, movement of the actuating elements 70 is achieved through an electronically controlled clutch-type mechanism, as will be described in further detail below.

In the preferred embodiment, the transfer device actuator system 40 includes an actuator plate 60 fixed to a linear drive 62, such as a pneumatic actuator, via one or more piston rods 64 or other form of connection for reciprocally translating the actuator plate in the z-direction. The linear drive 62 is preferably a pneumatic cylinder connected to inlet and outlet air lines and in electrical communication with the central control unit 24. The actuator plate 60 includes a plurality of individually activated electromagnets 61 fixed thereon. The number and arrangement of the electromagnets 61 preferably matches the number and arrangement of pins 37, 47 in the multi-pin array 46. The electromagnets 61 each include an interior bore to translatably receive an actuator rod 66 having the actuating element 70 attached at an end thereof.

Figure 6:
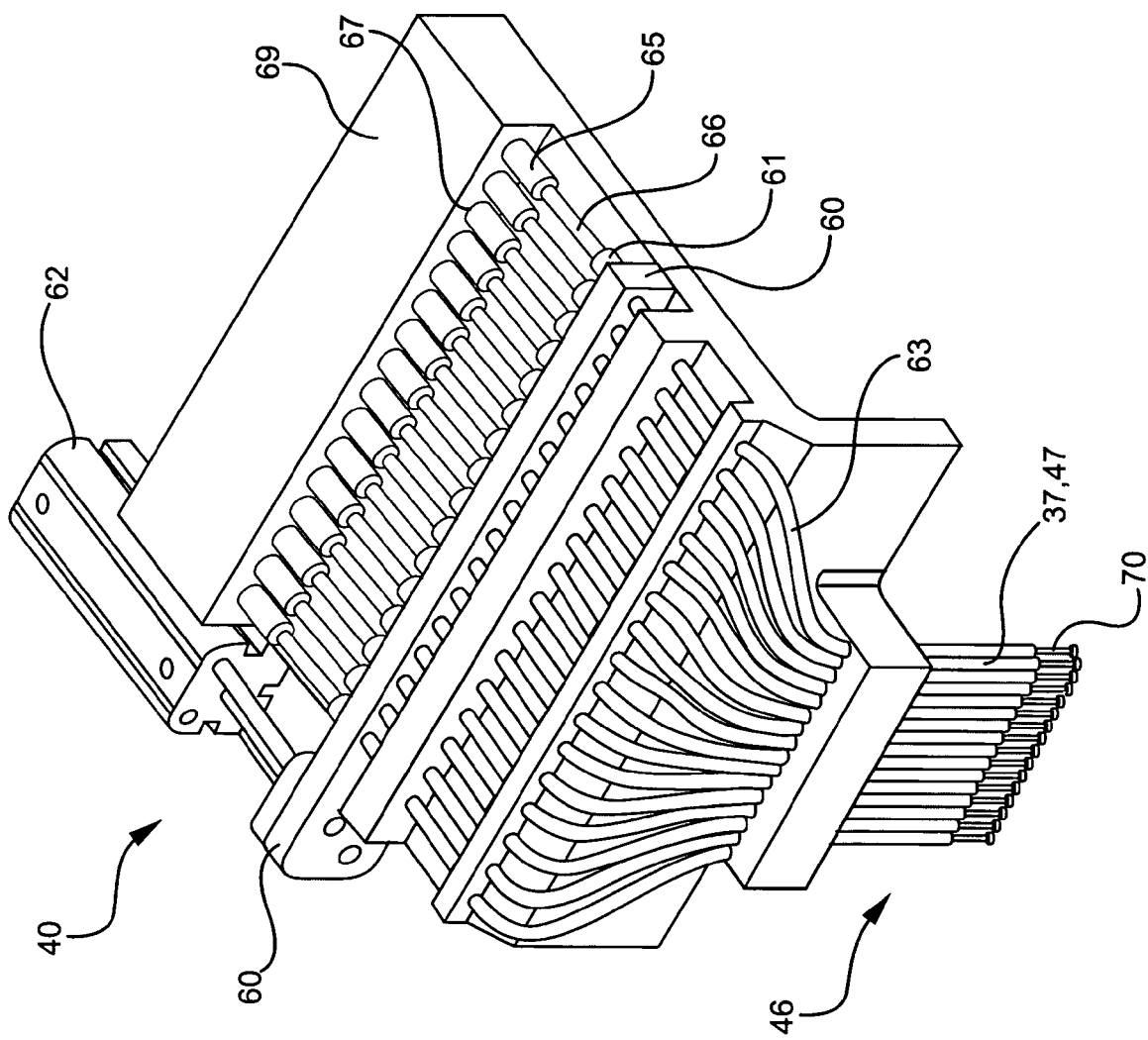
FIG. 6 is a top perspective view of an alternative embodiment of the magnet rod actuator system of the primary magnet unit.

The actuator rod 66 may be a semi-rigid tubular member oriented vertically with respect to the pins 37, 47, as shown in FIG. 5, or the rod may take the form of a flexible cable enclosed in a flexible cable guide 63, allowing for more condensed and angular orientations of the actuator system 40, as shown in FIG. 6. In both embodiments, at their ends opposite the actuating element 70, the actuator rods 66 are each fixed to a ferromagnetic piston 65 slidably received in a respective bore 67 of a piston housing 69. Also disposed in each bore 67 of the piston housing 69 is a tension spring 71 connected between the housing and the ferromagnetic piston 65 to maintain the actuator rod 66 in an upward retracted position.

In operation, the individual transfer devices 37 to be activated are preferably selected with the control unit 24. Alternatively, selection may be made via a control pad 68 disposed on the piston housing 69. The control pad 68 may be fixed to the piston housing 69, as shown in FIG. 4, or it may be provided on the frame 12 or other convenient location. The respective electromagnets 61 for the selected devices/pins 37, 47 may be electrically activated, whereby an attractive magnetic force is imposed on the selected electromagnets. Specifically, the linear drive 62 is activated to bring the actuator plate 60, along with the energized electromagnets 61, toward the ferromagnetic pistons 65 disposed in the piston housing 69. As the actuator plate 60 nears the piston housing 69, the energized electromagnets 61 attract their respective ferromagnetic pistons 65 drawing the pistons into contact with the electromagnets against the tension force of the spring 71.

The linear drive 62 is then reversed wherein the actuator plate 60 is driven away from the piston housing 69 in the z-direction. As the actuator plate 60 moves away from the piston housing 69, only those ferromagnetic pistons 65 that have been magnetically drawn into contact with a respective electromagnet 61 are moved together with the actuator plate. In this regard, the magnetic force applied by the electromagnets 61 is greater than the tension force applied by the tension springs 71 so that the selected ferromagnetic pistons 65 will move together with the actuator plate 60. This movement, in turn, moves the actuating element 70 disposed at the opposite end of the actuator rod 66 toward the tip of its respective pin, thereby applying a magnetic force at the tip.

The remaining non-selected pistons 65 maintain their original positions within with the piston housing 69 by virtue of the tension force applied by the tension springs 71. Thus, the actuating elements 70 in the respective pins 47 of the non-selected pistons 65 will not move toward the pin tip, thereby leaving these tips without a magnetic force.

Figure 7:
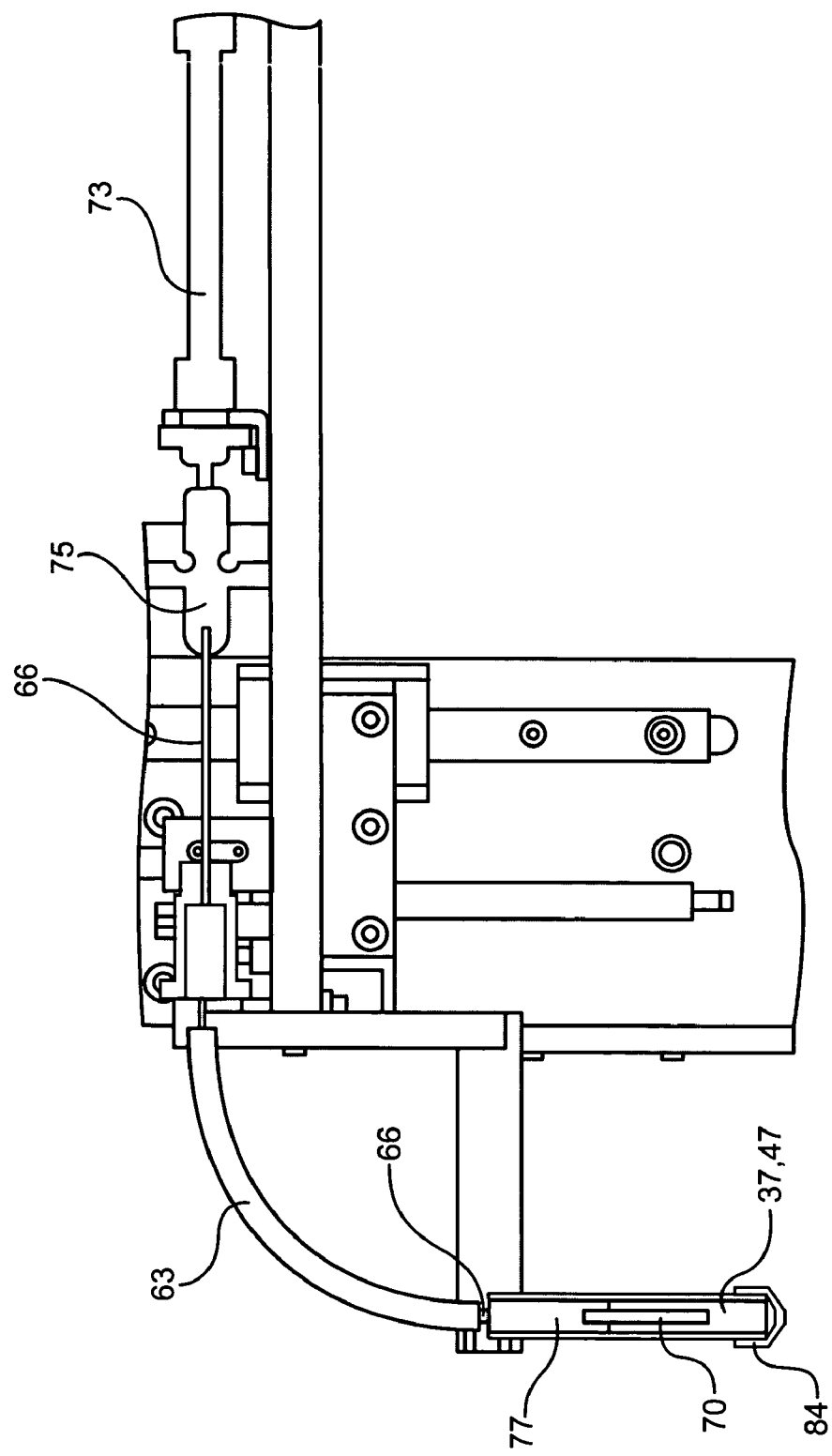
FIG. 7 is a cross-sectional view of still another alternative embodiment of the magnet rod actuator system of the primary magnet unit.

FIG. 7 shows yet another alternative embodiment for achieving this "combinatorial" technique. In this embodiment, rather than using an electromagnet clutch-type mechanism, as described above, each actuator rod 66 is coupled to its own individually activated rod drive 73 via a piston 75. The remaining components are the same in that a cylindrical actuating element 70, such as a magnet, is slidingly disposed in a respective pin 47 and the magnet is connected to an actuator rod 66, which in this case is preferably a flexible cable encased within a flexible cable guide 63. A magnet or iron piston 77 may be provided between the magnet 70 and the flexible rod 66 to improve stability. The rod drive 73 may be a pneumatic linear drive-type cylinder, as described above, and is preferably controlled by the system controller 24 to selectively drive the rod 66 to move the magnet 70 toward and away from the pin tip 84 to alternately apply and remove the magnetic force.

The present invention contemplates the use of any one of the combinatorial techniques described herein for the primary magnet unit 18 and, as will be discussed in further detail below, for the secondary magnet unit 20. Also, as mentioned above, the system of the present invention would also work to individually control the primary magnet combinatorial technique described in U.S. Pat. No. 6,409,925 to Gombinsky et al.

Figure 8:
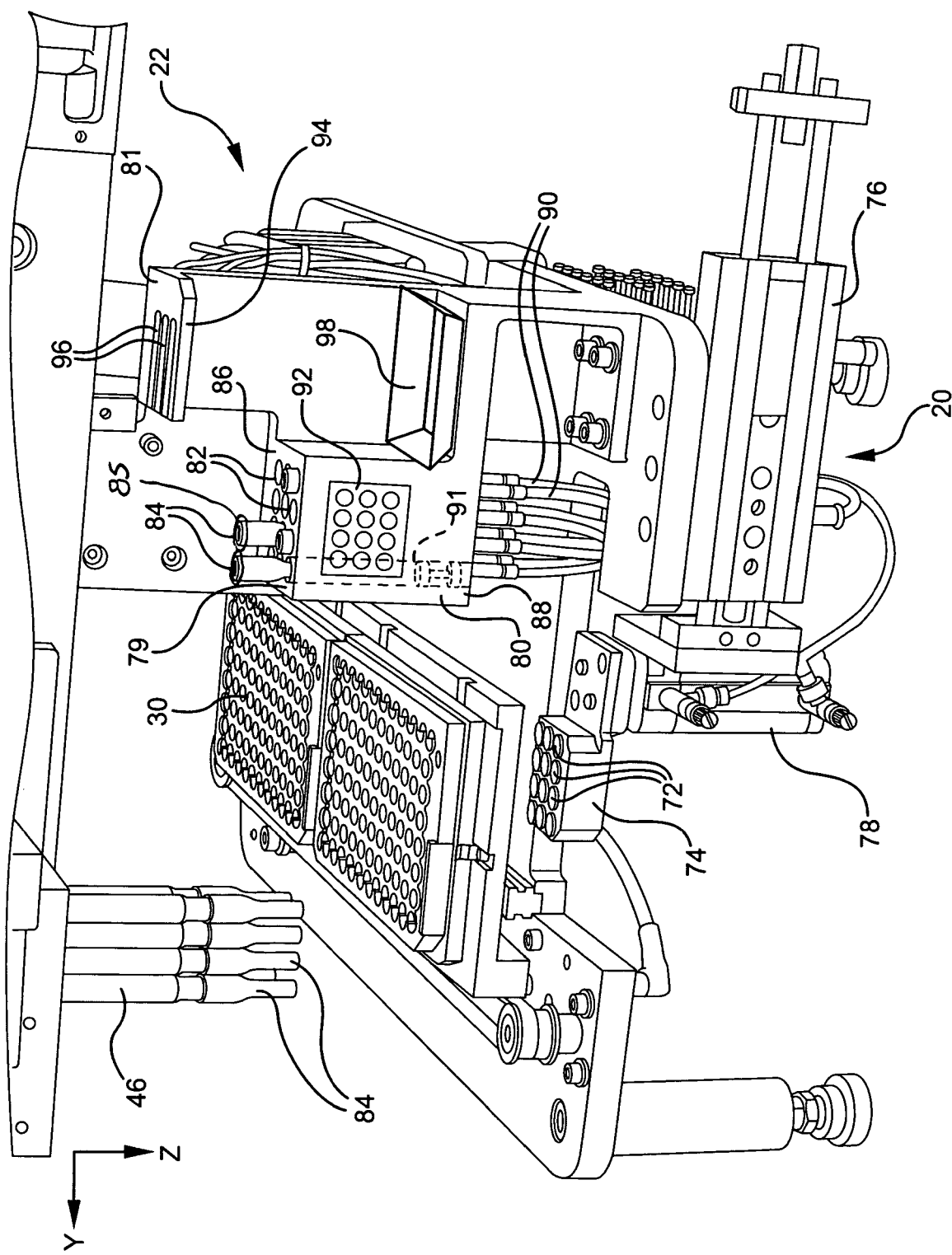
FIG. 8 is a top perspective view of the system shown in FIG. 1, with the secondary magnet unit, the tip insertion/removal station shown in greater detail.

Returning now to FIG. 3, and referring additionally to FIG. 8, in one embodiment, the secondary magnet unit 20 includes an array of secondary magnet elements, such as permanent magnets 72 fixed on a movable secondary magnet plate 74. The spacing and arrangement of the permanent magnets 72 generally coincides with the spacing and arrangement of the array 46 of pins 47 of the primary magnet unit 18. Thus, in the drawings, a 4×3 array of twelve permanent magnets 72, matching the spacing and arrangement of the pins 47, is provided in the secondary magnet plate 74. A y-axis magnet plate drive 76 and a z-axis magnet plate drive 78 are connected to the secondary magnet plate 74 to respectively, reciprocally translate the magnet plate in the y and z-directions. The magnet plate drives 76 and 78 are preferably pneumatic cylinders connected to inlet and outlet air lines and in electrical communication with the central control unit 24.

In operation, the magnet plate 74 is controlled to move in a complementary manner with the movement of the pin array 46 of the primary magnet unit 18. Briefly, the magnet plate 74 is fixed in the x-direction in aligned orientation with the magnet pin array 46 and will generally translate together with the pin array in the y-direction so that each well of the microtray 30 having a pin positioned thereover will also have a permanent magnet 72 positioned therebelow. Moreover, as will be described in further detail below, the magnet plate 74 is also controlled to complement the movement of the magnet rods 66 in the z-direction within the pin array 46 to facilitate removal or "washing" of the magnetic particles from the pin tips. This "washing" technique is also described in U.S. Pat. No. 6,409,925 to Gombinsky et al., the disclosure of which is incorporated herein by reference.

Alternatively, the secondary magnet plate 74 can be fixed in the z-direction and the permanent magnets 72 can be replaced with electro-magnets which are selectively activated and de-activated for the alternate application of a magnetic field on the magnetic particles in the wells of the micro-plate 30.

As mentioned above, in the preferred embodiment, the secondary magnet unit can be designed similar to the primary magnet unit 18, wherein individual secondary magnet rods can be selected in a manner similar to the primary magnet unit. Referring now to FIG. 9, which is a schematic diagram showing the functional components of the preferred embodiment of a secondary magnet unit 20', the secondary magnet plate 74 in this case includes an array of cylindrical bores 100 supporting a corresponding array of slidable secondary magnet rods 102, each having a magnet 104 fixed to a distal end thereof. Like the array of permanent magnets 72 described above, the array of slidable magnet rods 102 preferably matches, in number and arrangement, the array of pins 47 of the multi-pin array 46.

With the magnet plate 74 positioned below the micro-well tray 30 by the y- and z-drives 76 and 78, as described above, the magnet rods 102 are selectively controlled by a secondary magnet actuator 106. When a magnet rod 102 is fully inserted into its respective bore 100, a magnetic field is applied to attract the magnetic particles 39 suspended in the liquids 41 contained in the wells 43 of the micro-well tray 30 adjacent the inserted magnet rod. When the magnet rod 102 is retracted or withdrawn, the magnet 104 moves away from the bottom of the micro-well tray 30, thereby releasing the magnetic particles 39 free at the bottom of the well 43, ready to be picked up (or not) by a specifically chosen pin tip 49.

As mentioned above, individual movement of the magnet rods 102 with respect to the secondary magnet plate 74 is controlled by the secondary magnet actuator 106. Again, such movement can be achieved pneumatically, wherein each cylindrical bore 100 in the magnet plate 74 is connected to air lines for the supplying and release of pneumatic forces to move the magnet rods 102 as desired. However, in a preferred embodiment, the secondary magnet unit 20' utilizes an electromagnetic clutch-type mechanism, as described above with respect to the primary magnet unit 18 and as shown in FIG. 10.

Specifically, as shown in FIG. 10, the secondary magnet actuator 106 generally includes an actuator plate 108 fixed to a linear drive 110, such as a pneumatic actuator, via one or more piston rods 114 or other form of connection for reciprocally translating the actuator plate in the z-direction. The linear drive 110 is preferably a pneumatic cylinder connected to inlet and outlet air lines and in electrical communication with the central control unit 24. The actuator plate 108 includes a plurality of individually activated electromagnets 116 fixed thereon. The number and arrangement of the electromagnets 116 matches the number and arrangement of secondary magnets 104 of the secondary magnet unit 20'. The electromagnets 116 each include an interior bore 118 to translatably receive a respective secondary magnet rod 102 having a secondary magnet 104 attached at an end thereof.

The magnet rod 102 may be a semi-rigid tubular member oriented vertically with respect to the pins 47, as shown in FIG. 10, or the rod may take the form of a flexible cable enclosed in a flexible cable guide allowing for more condensed and angular orientations of the actuator system. In any event, at their ends opposite the magnet 104, the magnet rods 102 are each fixed to a ferromagnetic piston 120 slidably received in a respective bore 122 of a piston housing 124. Also disposed in each bore 122 of the piston housing 124 is a tension spring 126 connected between the housing and the ferromagnetic piston 120 to maintain the magnet rod 102 in a downward retracted position.

In operation, application of a magnetic force to individual wells 43 of the micro-well plate 30 may be selected via a control pad 128 disposed on the piston housing 124. The respective electromagnets 116a for the selected secondary magnets 104 are then electrically activated, whereby an attractive magnetic force is imposed on the selected electromagnets. The linear drive 110 is then activated to bring the actuator plate 108, along with the energized electromagnets 116, toward the ferromagnetic pistons 120 disposed in the piston housing 124. As the actuator plate 108 nears the piston housing 124, the energized electromagnets 116a attract their respective ferromagnetic pistons 120a drawing the pistons into contact with the electromagnets against the tension force of the spring 126.

The linear drive 110 is then reversed wherein the actuator plate 108 is driven away from the piston housing 124 in the z-direction. As the actuator plate 108 moves away from the piston housing 124, only those ferromagnetic pistons 120a that have been magnetically drawn into contact with a respective electromagnet 116a are moved together with the actuator plate. In this regard, the magnetic force applied by the electromagnets 116a is greater than the tension force applied by the tension springs 126 so that the selected ferromagnetic pistons 120a will move together with the actuator plate 108. This movement, in turn, moves the secondary magnet 104 disposed at the opposite end of the magnet rod 102 toward the micro-well plate 30, thereby applying a magnetic force at the adjacent well 43.

The remaining non-selected pistons 120b maintain their original positions within the piston housing 124 by virtue of the tension force applied by the tension springs 126. Thus, the magnets 104 of the non-selected pistons 120b will not move toward the micro-well tray 30, thereby leaving these adjacent wells 43 without a magnetic force.

In all of the above embodiments, movement in the z-direction of the secondary magnets 72 or 104 below the micro-well plates 30, in conjunction with movement in the z-direction of the multi-pin head 46 has the desired effect of removing or "washing" the magnetic particles 39 from the pin tips. This so called "washing" involves the dipping and raising of the pins 47 into and out of the wells 43 of the micro-plate 30 both with and without the magnetic rods 66 inserted into the pins. The secondary magnets 72 or 104 can also be selected with regard to size and strength so that the described up and down motion will create a concentrated "button" of separated magnetic particles 39 to gather at the bottom of the selected wells 43.

Returning to FIG. 8, the tip insertion/removal station 22 will now be described. In general, the tip insertion/removal station includes a tip insertion unit 79 for applying the disposable tips 84 to the ends of the pins 47 of the multi-pin array 46 and a tip removal unit 81 for removing the tips from the pins after use.

The tip insertion unit 79 generally includes a manifold block 80 fixed to the system frame 12 and having an array of cylindrical bores 82 formed therethrough. The spacing and arrangement of the bores 82 coincides with the spacing and arrangement of the pins 47 within the pin array 46 of the primary magnet unit 18. Thus, in the drawings a 4×3 array of twelve cylindrical bores 82, matching the spacing and arrangement of the pins 47, is provided in the manifold block. The cylindrical bores 82 are also sized to respectively receive a disposable protective tip 84 which is insertable and removable from a respective pin 47 of the primary magnet unit 18.

The tips 84 are loaded into the cylindrical bores 82 at the top face 86 of the manifold block 80 so that their tapered ends point downward.

The manifold block 80 may be loaded manually with a plurality of pin tips 84 or the tip loading may be automated either by feeding single pin tips into the cylindrical bores 82 or by exchanging a complete manifold block with pin tips pre-loaded. For example, the pin tips 84 may be marshaled from a batch, wherein single oriented tips are fed to respective cylindrical bores 84 in the block 80, by a conventional vibratory feeder connected to the manifold block. Alternatively, the entire manifold block 80 with spent tips 84 can be exchanged with a new block by a small robot. In this manner, the block 80 can be pre-loaded away from the system and kept sterile until just prior to use. This method further eliminates down time of the system for loading tips. In either case, the system is thus provided with a higher efficiency.

Connected to each cylindrical bore 82 at the bottom face 88 of the manifold block 80 is an air supply line 90 connected at its opposite end to an air supply source (not shown) for supplying at least a positive air pressure to the cylindrical bore. Furthermore, a tip loading piston 91 is slidably disposed within each cylindrical bore 82 to force the tips 84 onto their respective pins 47 during tip insertion. Preferably, selection of the tips to be loaded is made via the central control unit 24. Alternatively, a tip selection control pad 92 can be provided on the manifold block 80 to select which tip loading pistons 91 within the cylindrical bores 82 are to be activated with air pressure. The air stream is preferably guided through a special tube to prevent contamination of tips and plates.

The air supply line 90 and air supply source may be configured to also provide a negative pressure or vacuum to the cylindrical bore 82 to aid in tip removal from the pins 47. In such a case, the bore 82 must be cleaned and disinfected prior to reloading with clean tips.

Alternatively, the tip insertion/removal unit 22 may further include a tip removal fork 94 attached to the manifold block 80 or to the system frame. The tip removal fork 94 includes a plurality of open channels 96 facing in the y-direction toward the pin array 46 of the primary magnet unit 18. The number of channels 96 provided in the fork 94 corresponds to the number of rows of pins 47 oriented in the y-direction of the pin head 46. The width of the channels 96 is slightly larger than the diameter of the pins 47, but slightly smaller than an upper rim 85 of the disposable plastic tips 84 inserted on the pins.

In operation, the manifold block 80 is first manually or automatically loaded with a plurality of pin tips 84. Alternatively, a new pre-loaded block 80 can be installed on the system frame 12. The pin array 46 of the primary magnet unit 18 is positioned above the manifold block by the y and z stepper motors 42 and 44 and then gently brought down in the z-direction until the ends of the pins 47 are in close proximity to the disposable tips 84. The desired tips 84 can then be entered in the control unit 24, whereby a burst of air pressure supplied by the respective air lines 90 will drive the selected tip loading pistons 91 upwardly to frictionally engage the tips 84 onto the pins 47. To release the air, so that the tips will not become contaminated, a special tube is connected to the bore 82 beneath piston 91 when at its upper position.

For removal of tips 84 from the pins 47, a negative pressure or vacuum can be provided through the air line 90 for pulling the tips off the pins when the pin array 46 is positioned over the manifold block 80. However, in the preferred embodiment, a separate tip removal unit 81 is provided. The tip removal unit 81 includes a tip removal fork 94 having a plurality of channels 96 generally matching in width to the diameter of the pins 47 of the pin array 46. The pin array 46 is brought into engagement with the tip removal fork 94, whereby individual rows of pins 47 are received within the channels 96 of the fork and such that the tips 84 are positioned below the fork. The pin array 46 is then elevated in the z-direction, whereby the fork 94 will contact the upper rim of the tips 84 preventing the tips from moving further along with their respective pins 47. A tip receptacle 98 can be provided below the tip removal fork 94 to catch the tips 84 removed from the pins 47 in this manner.

The last major functional component of the multi-pin system 10 of the present invention is the central control unit 24. The central control unit 24 is generally a programmable controller that coordinates all movements and actuations of the system. preferably, the central control unit 24 controlling the system includes a programmable logic controller (PLC) with a human machine interface (HMI) and a position controller, which may be provided directly on the frame 12 or be remotely located. The control system not only handles the positioning task of moving the multi-pin head 46 to selected regions or zones within a selected micro-plate, it also provides the operator with the option to select a user defined combination of pins 47 for the process. Execution of all sub-processes can also be initiated individually or the entire magnetic separation process can be executed via the control system 24. All required user parameters/specifications for each the above mentioned processes are defined by the operator via the HMI.

In a preferred embodiment, the control system 24 is a Programmable Logic Controller (PS1 Modular) together with a Front End display unit (FED-120C) as the HMI, supplied by Festo Corporation of Hauppauge, N.Y. The PS1 programmable logic controller communicates over a serial interface with a position controller (Festo SPC200), transferring the positioning data which controls the stepper motors. The Festo SPC200 is a modular position controller capable of both servo pneumatic control and stepper motor control. Three stepper motor cards are employed in the controller and the three axis system operates in open loop mode (without encoder feedback).

All operator settings are specified at the HMI device. The settings include specifying the x, y and z coordinates for a specific movement, a homing sequence, a setup menu where the number of cycles, combinatorial selection of tips, zones of the micro-plate to be used and the micro-plate selection. Other functions include a jogging function and an option to reset the system to default/factory settings.

Figure 11:
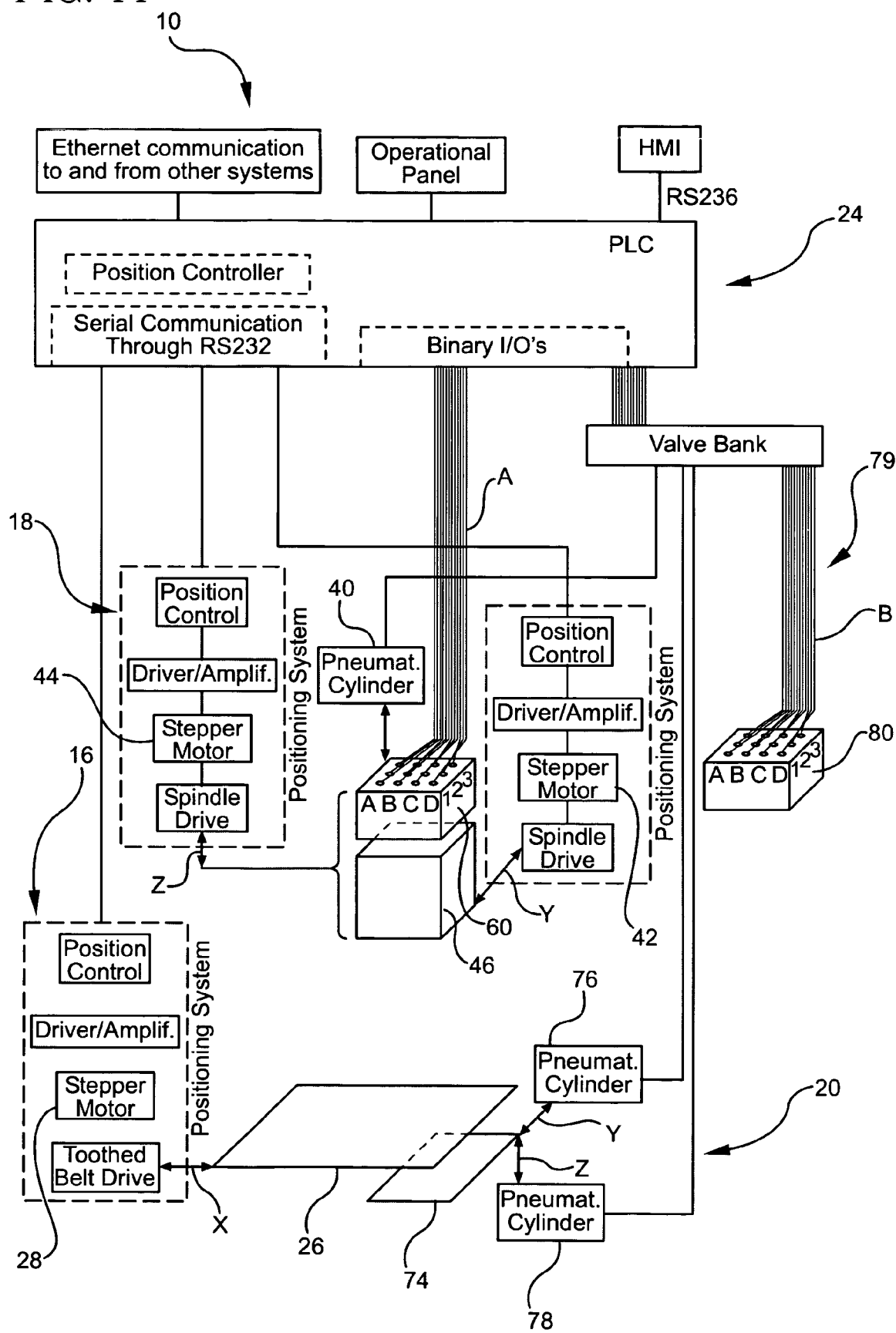
FIG. 11 is a block diagram of the overall system formed in accordance with the present invention.
Figure 12B:
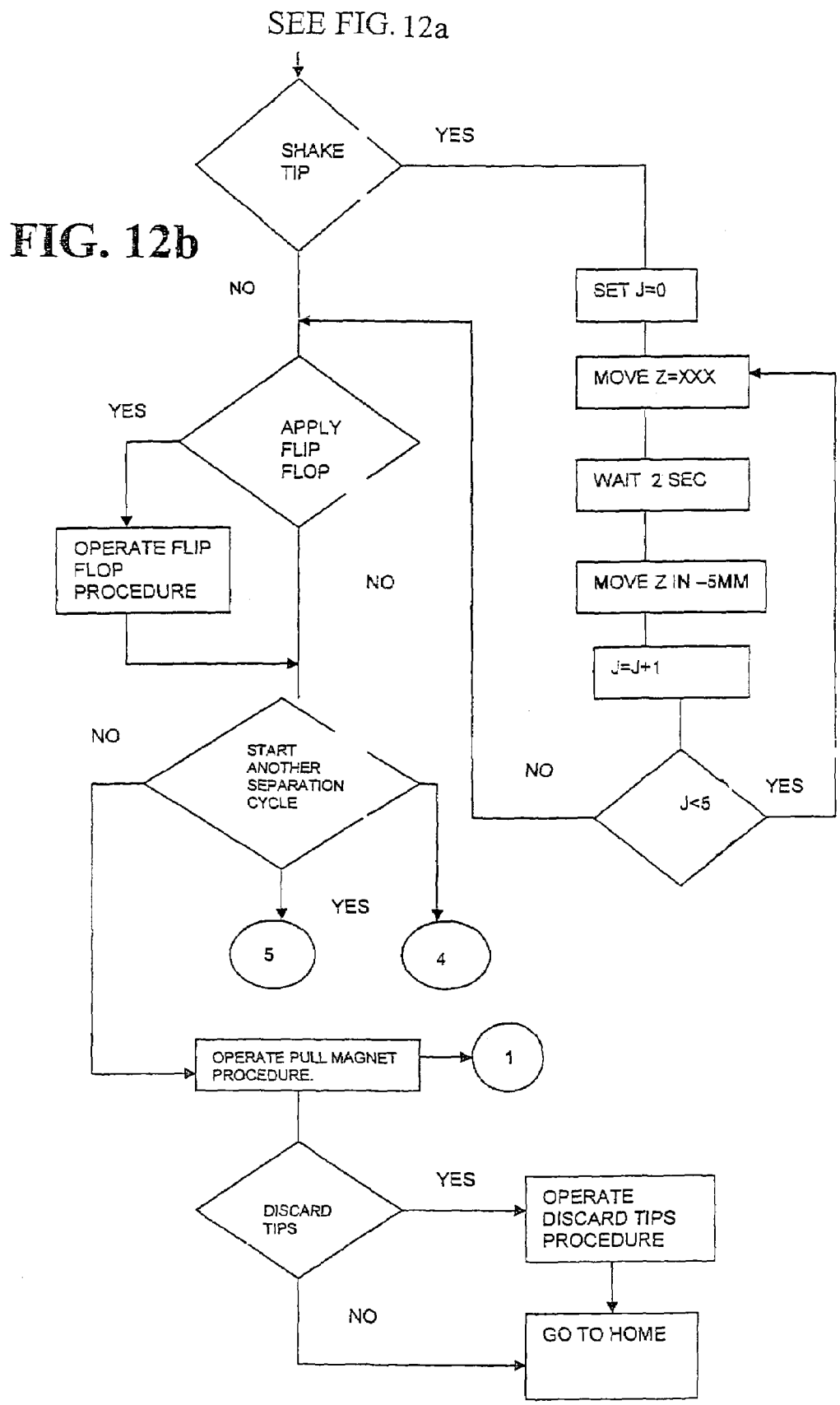
Figure 13:
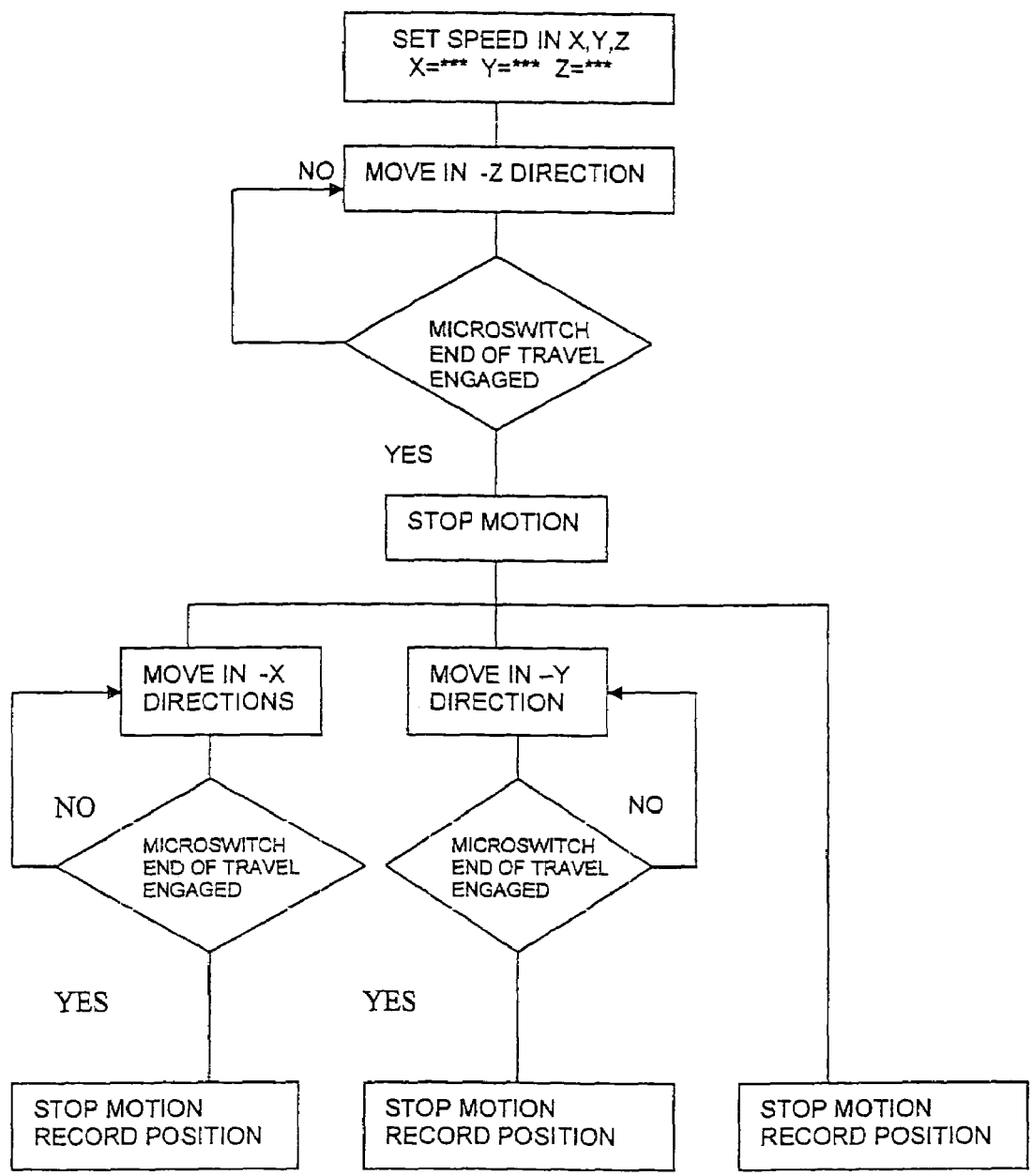
FIG. 13 is a flow chart of the homing procedure.

Referring now to FIG. 11, which is a block diagram of the overall system 10, and additionally to FIGS. 12*a* and 12*b*, which is an operational flow chart of the overall system, operation of the pin system will be described in further detail. On power up of the system 10, the operator is prompted to initialize (execute a reference run) the axes prior to proceeding with the main menu/entering of process parameters. Referring additionally to FIG. 13, the "homing process" involves the stepper motor controller executing a reference run on all three axes at a user defined speed. Limit or overtravel sensors 29 may be mounted on each end of each axis for use in the homing process. (See FIGS. 2 and 4.) Thus, "Home" can be defined by the limit switch 29 at the end of the axes where the motor is mounted.

Figure 14:
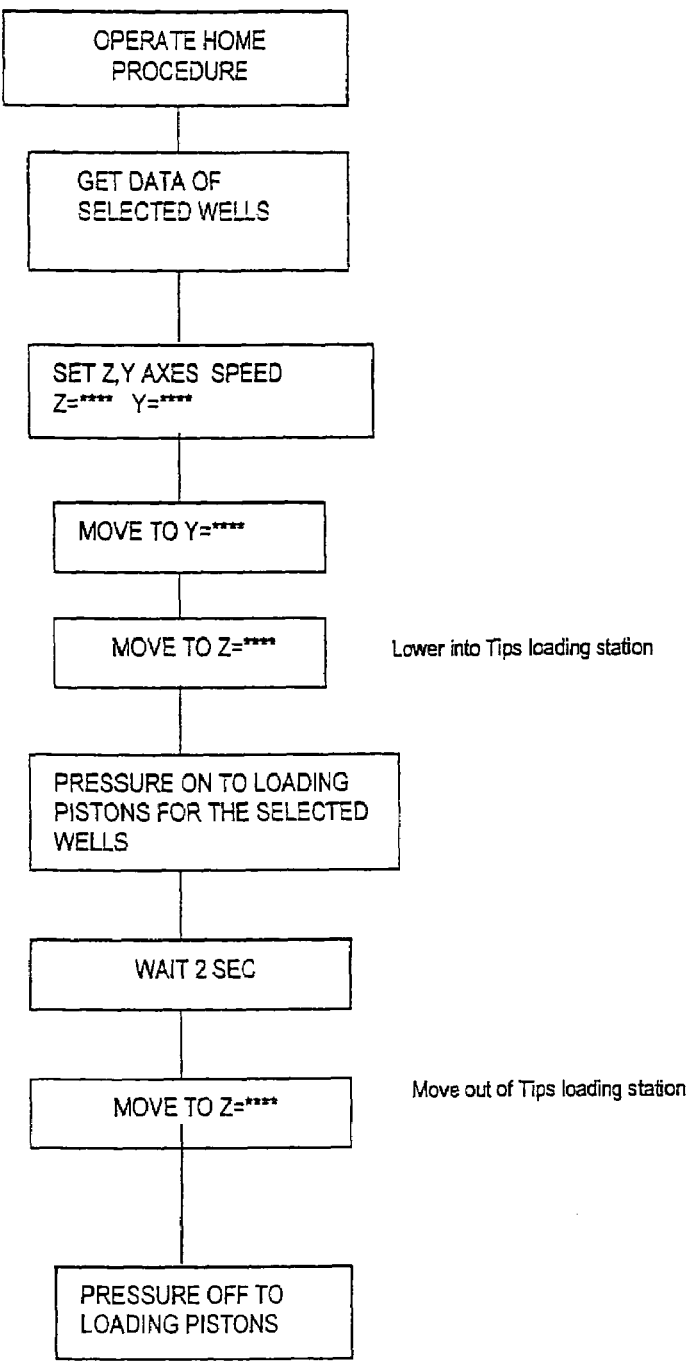
FIG. 14 is a flow chart of the tips loading procedure.

Referring to FIG. 14, the next sub-process that is executed in a complete separation cycle is the "tip loading process." The axes are preferably brought to their home positions prior to executing the loading of tips 84 on the pins 47. As mentioned above, the pins 47 to be loaded with tips will be specified on the HMI via the tip selection pad 92. The position coordinates of the tip loading station 79 are preferably preset and can not be changed by the operator. Once the multi pin head 46 is in position and lowered into the tip loading station 79, the tip loading pistons 91 (which initially reside at the bottom 88 of the bores 82 of the manifold block 80) corresponding to the selected pins are extended thereby loading the tips 84 firmly onto the selected pins 47. The multi-pin array 46 of the primary magnet unit 18 is then raised to its home position and the tip loading pistons 91 are retracted.

Figure 15:
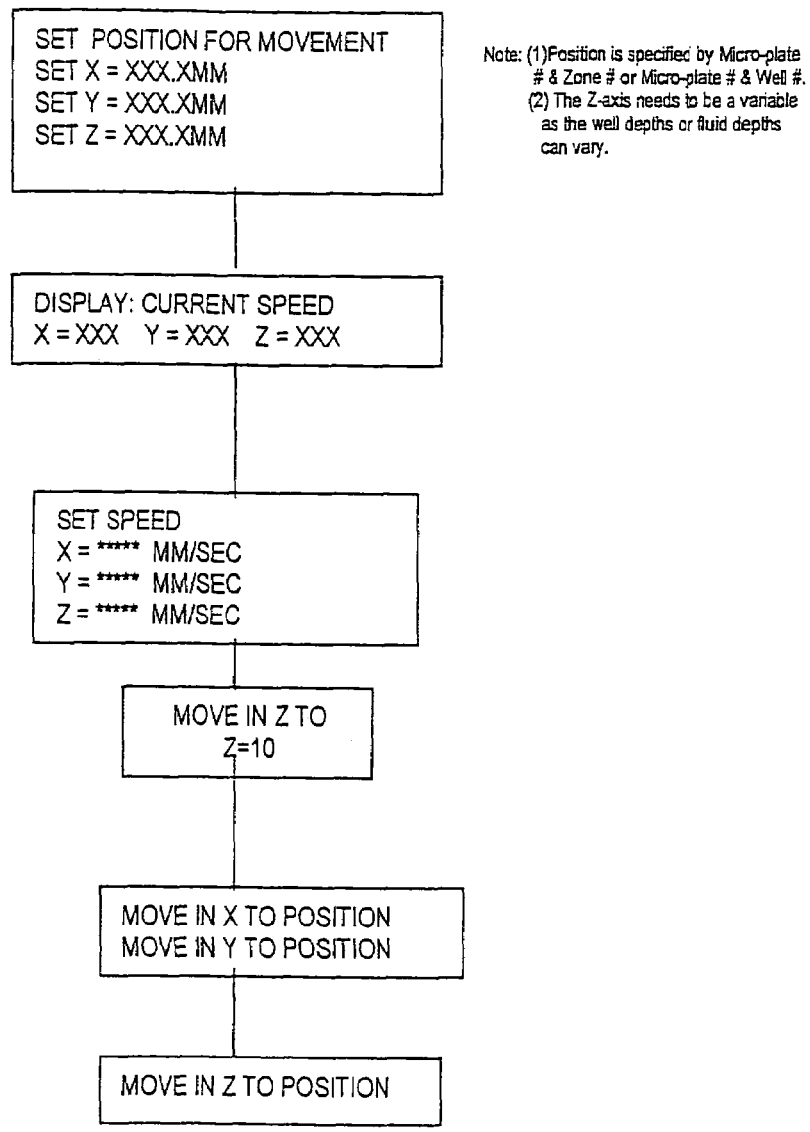
FIG. 15 is a flow chart of the xyz positioning procedure.

Once the tips 84 are loaded, the multi-pin head 46 will move to a specified zone on a selected micro-plate 30 by executing an xyz positioning sequence, as shown in FIG. 15, wherein the xy positioning is based on "Zone" or "Well" positions. Specifically, the micro-plate 30 is divided into a plurality of zones, each zone having a well array corresponding to the size and arrangement of the pin array 46. Thus, in the embodiment shown in the drawings, the micro-well plate 30 will be divided into a plurality of zones, wherein each zone has a 4×3 matrix of wells and an assigned location.

Prior to positioning, the operator is preferably prompted to select the tray number, zone within that tray and the corresponding wells within the zone. Based on the selected tray, zone and wells, the positioning coordinates for the x and y axis are calculated by the PLC and transferred to the position controller via the serial interface. Initializing the positioning task and coordinating the movements (interlocks) between the axes is achieved by using handshaking signals (Start/Motion complete) and discrete I/O signals of the position controller. Positioning instructions refer to the positions transferred to the position controller over the serial interface and instructions to be executed are selected using the discrete I/O (Record select mode).

The z-axis positioning of the multi-pin head 46 can be specified in millimeters (mm) by the operator as the well depth can differ from different micro-plate suppliers. Liquid levels can also vary within the wells. Moreover, the speeds for each axis can also be specified by the operator in mm/s.

The execution of the movement starts with the multi-pin head 46 retracting in the z-direction to a predefined (factory preset) position to ensure the pins 47 will clear the surface of the micro-plate 30. The micro-well drive unit 16 then positions the micro-well plate 30 in the x-direction while the y-motor 42 of the primary magnet unit 18 positions the multi-pin head 46 in the y-direction. The same positioning sequence applies to both moving the multi-pin head 46 to a sample micro-well tray and moving the head to a separate washing liquid tray. The sequences are preferably interlocked by the handshaking signals of the position controller.

Figure 16A:
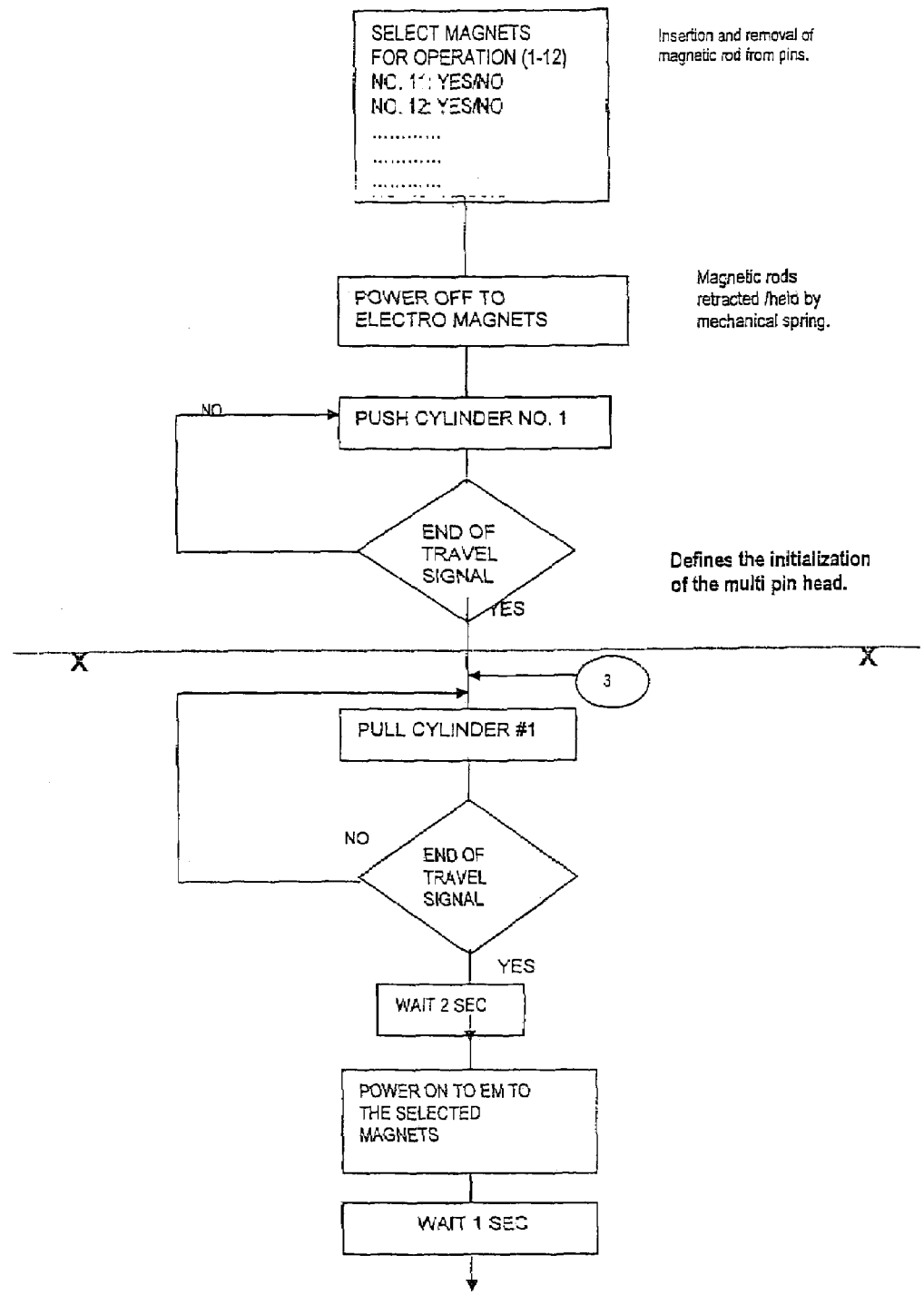
FIGS. 16a and 16b is a flow chart of the push/pull magnet procedure.
Figure 16B:
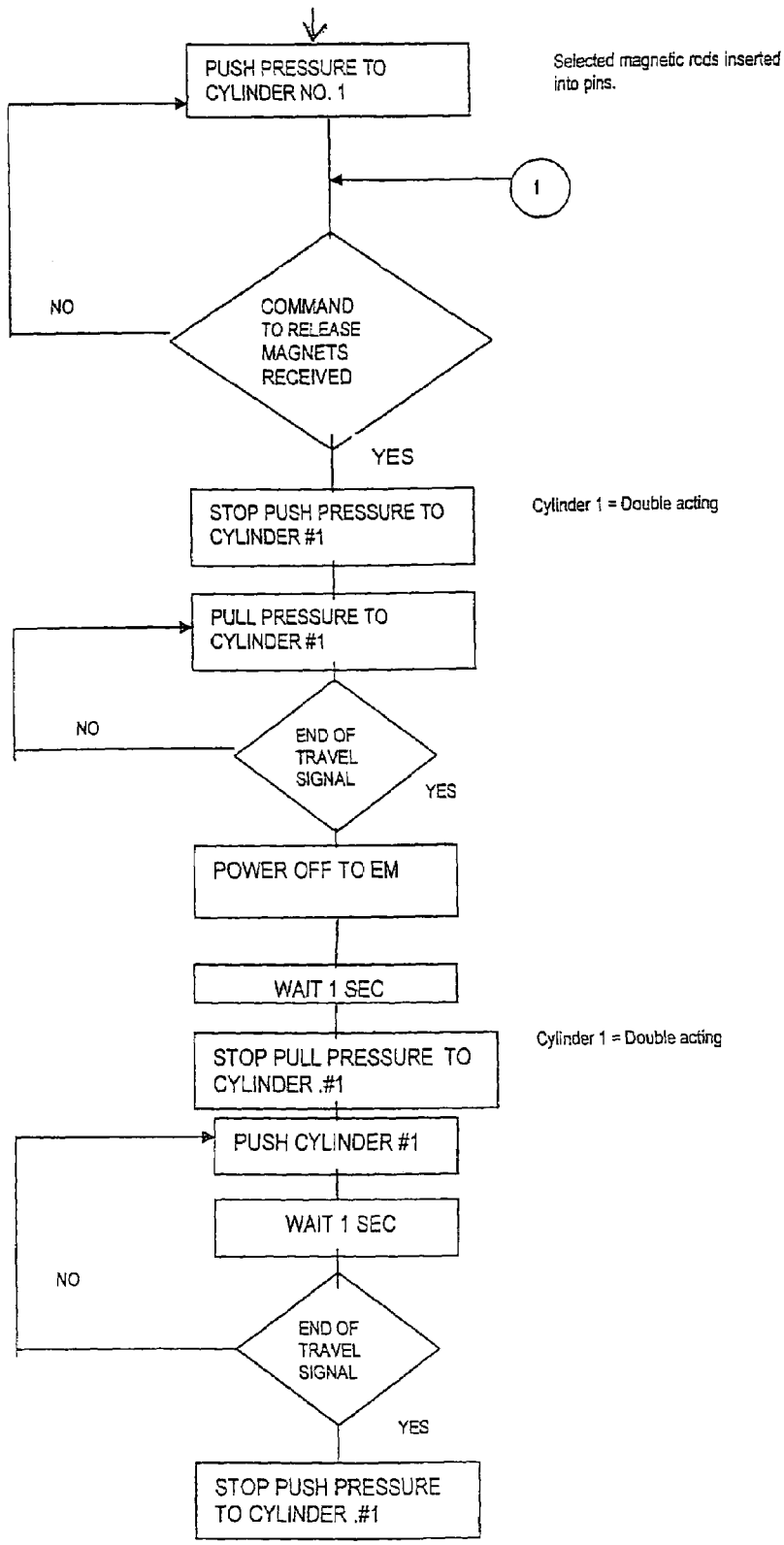

Referring now additionally to FIGS. 16*a* and 16*b*, the next sequence, termed the "push/pull magnet sequence" essentially involves the selection of pins 47 within the multi-pin head 46 and the insertion of the selected magnetic rods 66 into these pins by the multi-pin actuator 40. As described above, and shown in FIG. 5, in the preferred embodiment, this process is achieved by the actuation of the double acting cylinder 62 which lifts and lowers an actuator plate 60 having an array of electromagnets 61 provided thereon. The default state of the multi-pin head would be with the cylinder extended where the electromagnet array is held away from the mechanical coils 71 which hold the magnetic rods 66 in their default position.

The push/pull process is activated by retracting the double acting cylinder 62, raising the electromagnet array 61 towards the supporting piston housing 69. The selected electromagnets 61 draw their respective ferromagnetic pistons 65 out of the piston housing 69 (overcoming the mechanical spring force which keeps the magnetic rods 66 in their home position) and the rods are then inserted into the hollow pins 47.

The double acting cylinder 62 is also preferably fitted with two limit switches (not shown).

Figure 17A:
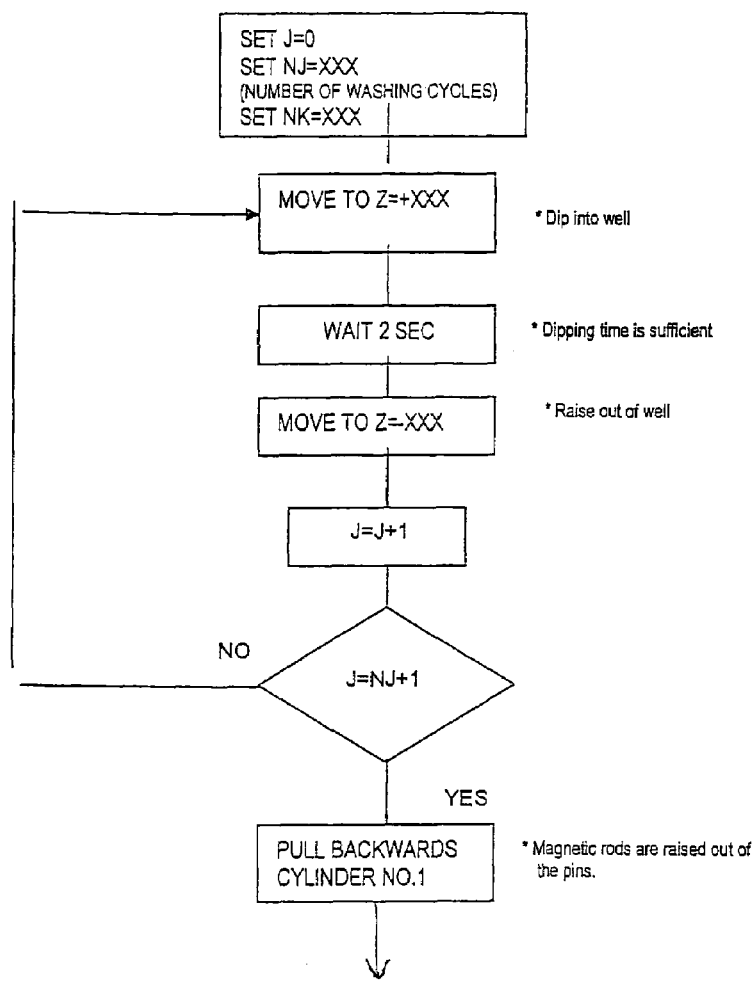
FIGS. 17a and 17b is a flow chart of the washing procedure.
Figure 17B:
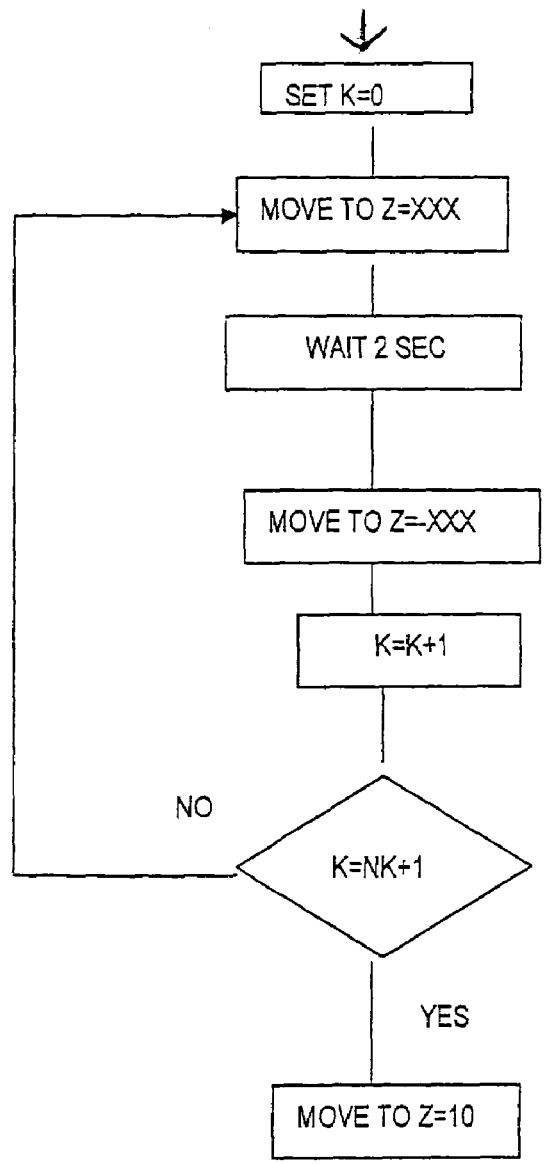

Referring now additionally to FIGS. 17*a* and 17*b*, the "washing procedure" generally involves the moving of the multi-pin head, with magnetic particles attached to the selected tips, to a target zone of the micro-well plate or to another plate altogether. Briefly, the multi-pin head 46 is moved in the z-direction to repeatedly dip and raise the pin tips 49, 84 into and out of the micro-wells containing a "washing" fluid therein. At the same time, the magnetic rods 66 are retracted from inside the pins 47, thereby removing the magnetic force from the tips. In this manner, the magnetic particles are released from the ends of the pins 47 and are captured by the "washing" fluid within the micro-wells.

Figure 18A:
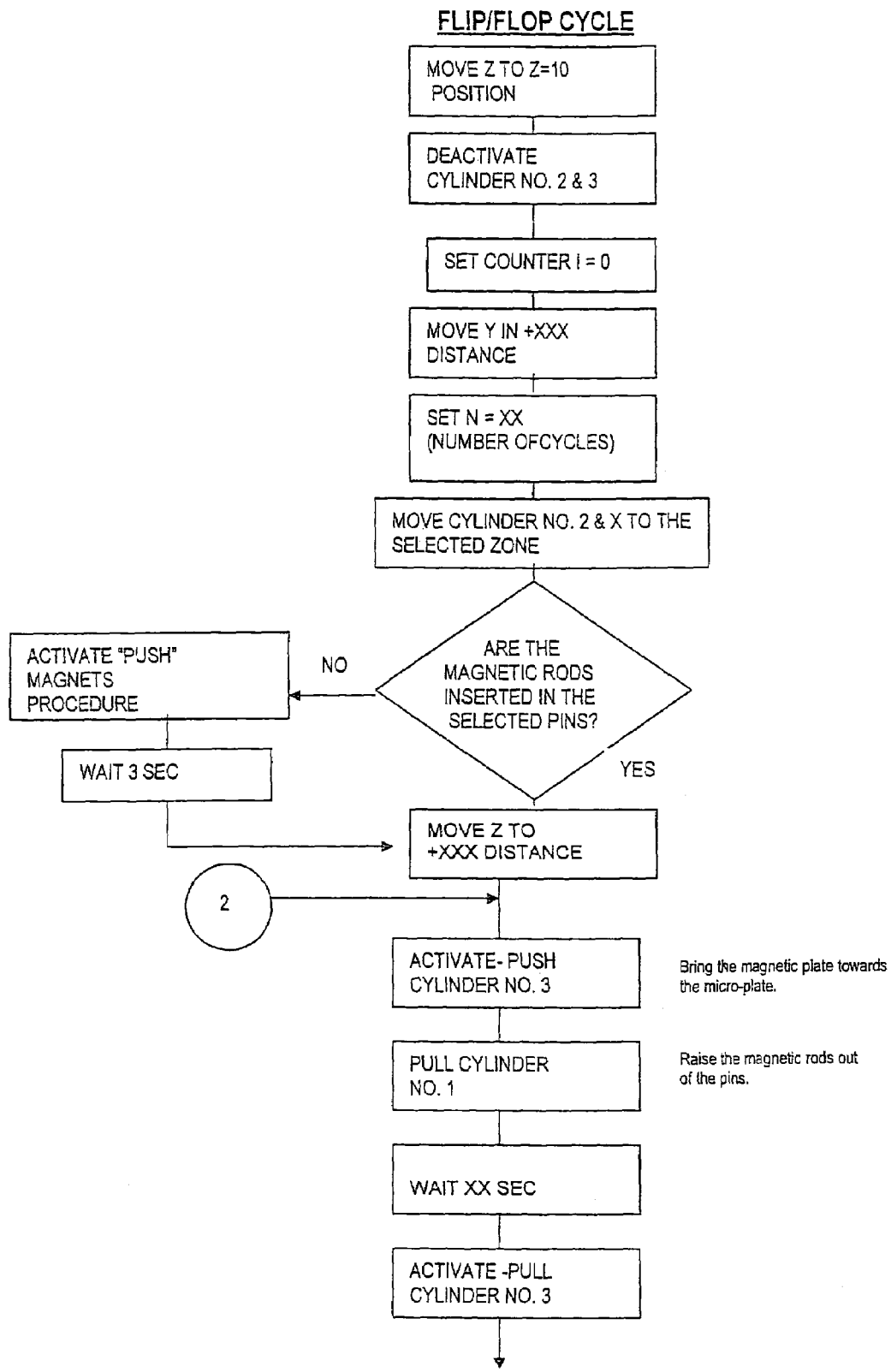
FIGS. 18a and 18b is a flow chart of the flip/flop cycle.
Figure 18B:
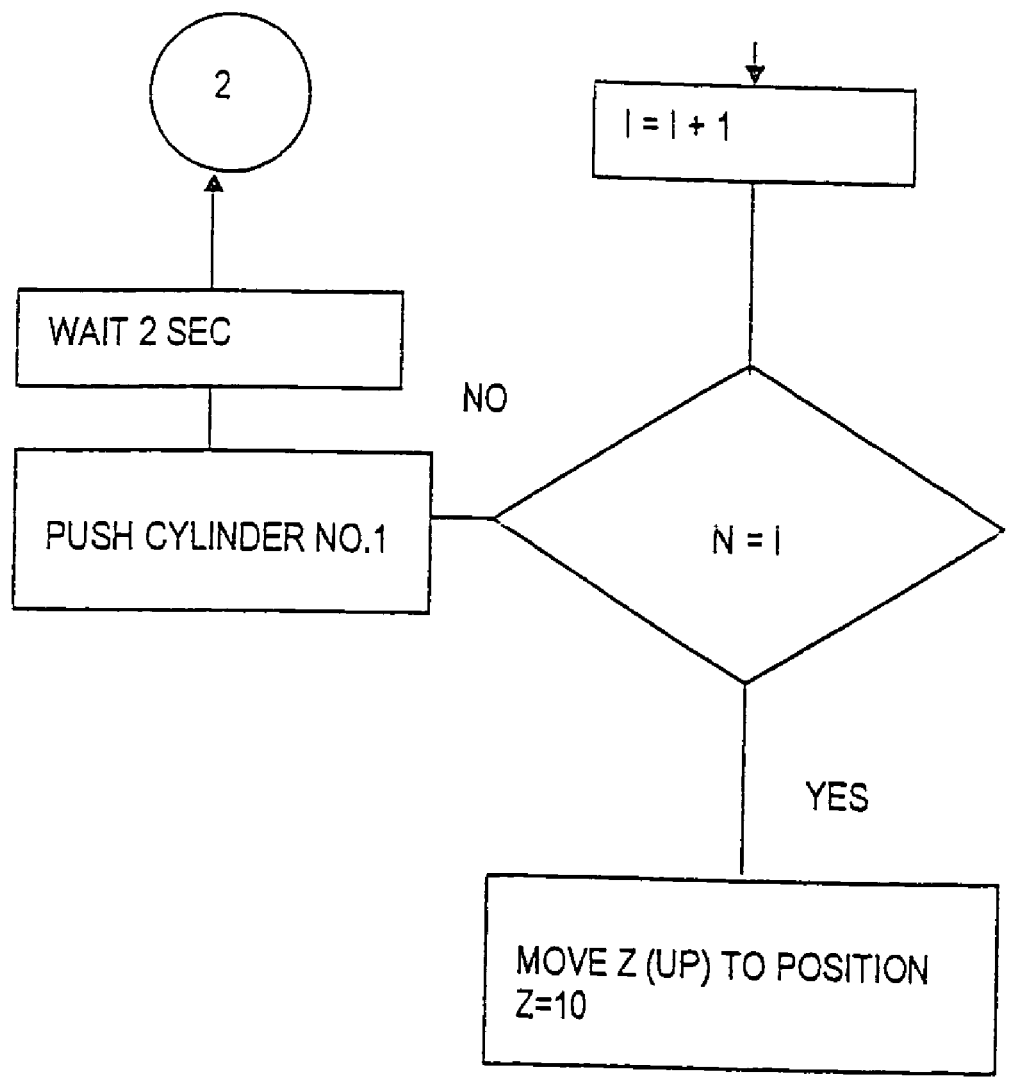

As discussed above, both the "push/pull" sequence and the "washing procedure" may further involve a "flip/flop cycle" which makes use of the secondary magnet unit 20. Referring now additionally to FIGS. 18*a* and 18*b*, the "flip/flop cycle" generally involves coordinated movement and actuation of the primary magnet unit 18 and the secondary magnet unit 20 from above and below the micro-well tray 30. Essentially, the secondary magnet unit 20 is brought up to the micro-well tray 30 as the primary magnet unit 18 is lifted upwardly away from the tray so that the magnets of the secondary magnet unit will help retain magnetic particles in the micro-well trays that have not been selected. As also discussed above, this process is further enhanced when the secondary magnet unit 20 is provided with "combinatorial" capabilities, wherein individual secondary magnets can be independently actuated, as described above and shown in FIG. 10.

Figure 19:
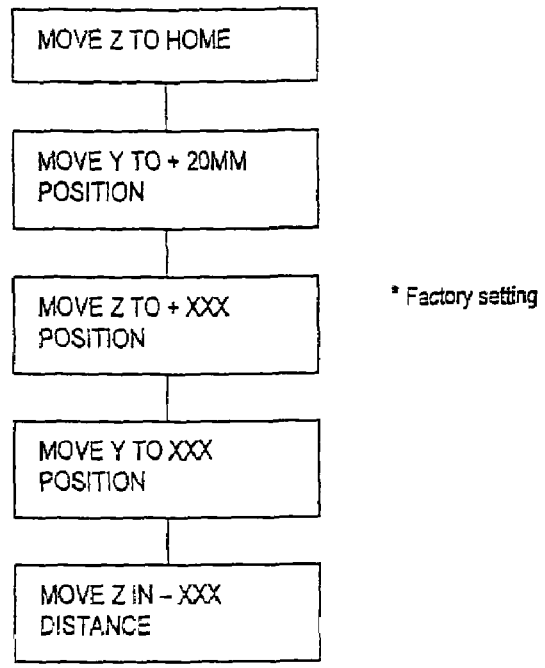
FIG. 19 is a flow chart of the tip discard procedure.

Once a magnet separation process is complete, the tip discard procedure can be initiated, as shown in FIG. 19. As discussed above, the tip discard procedure generally involves moving the multi-pin head 46 into engagement with the tip removal fork 94 and elevating the head in the z-direction, whereby the fork will disengage the tips from the pins to be captured in the tip receptacle 98.

Figure 20:
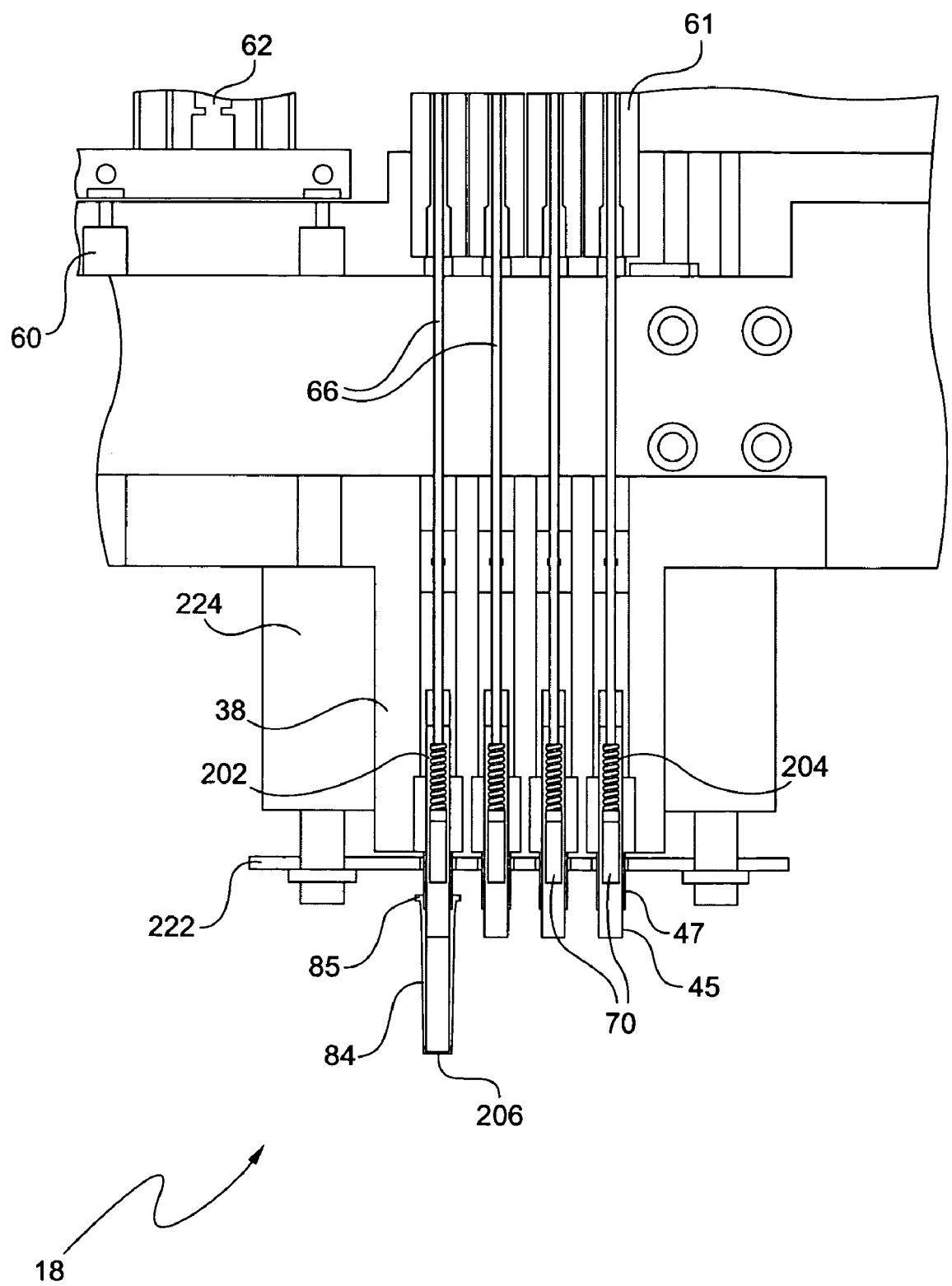
FIG. 20 is a cross-sectional view of the preferred embodiment of the primary magnet unit shown in further detail with the magnets in their up position.
Figure 21:
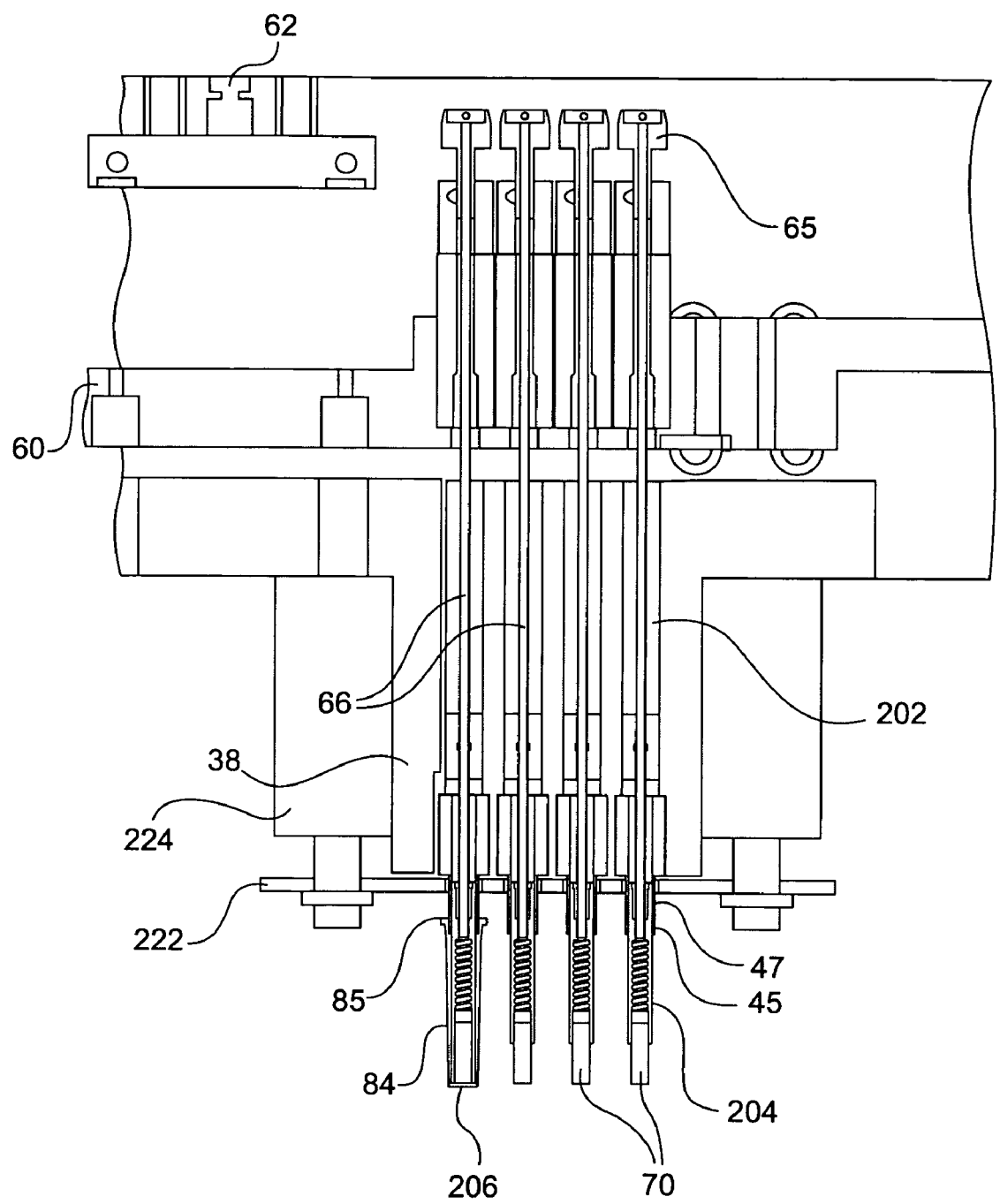
FIG. 21 is a cross-sectional view of the preferred embodiment of the primary magnet unit shown in further detail with the magnets in their down position.
Figure 22:
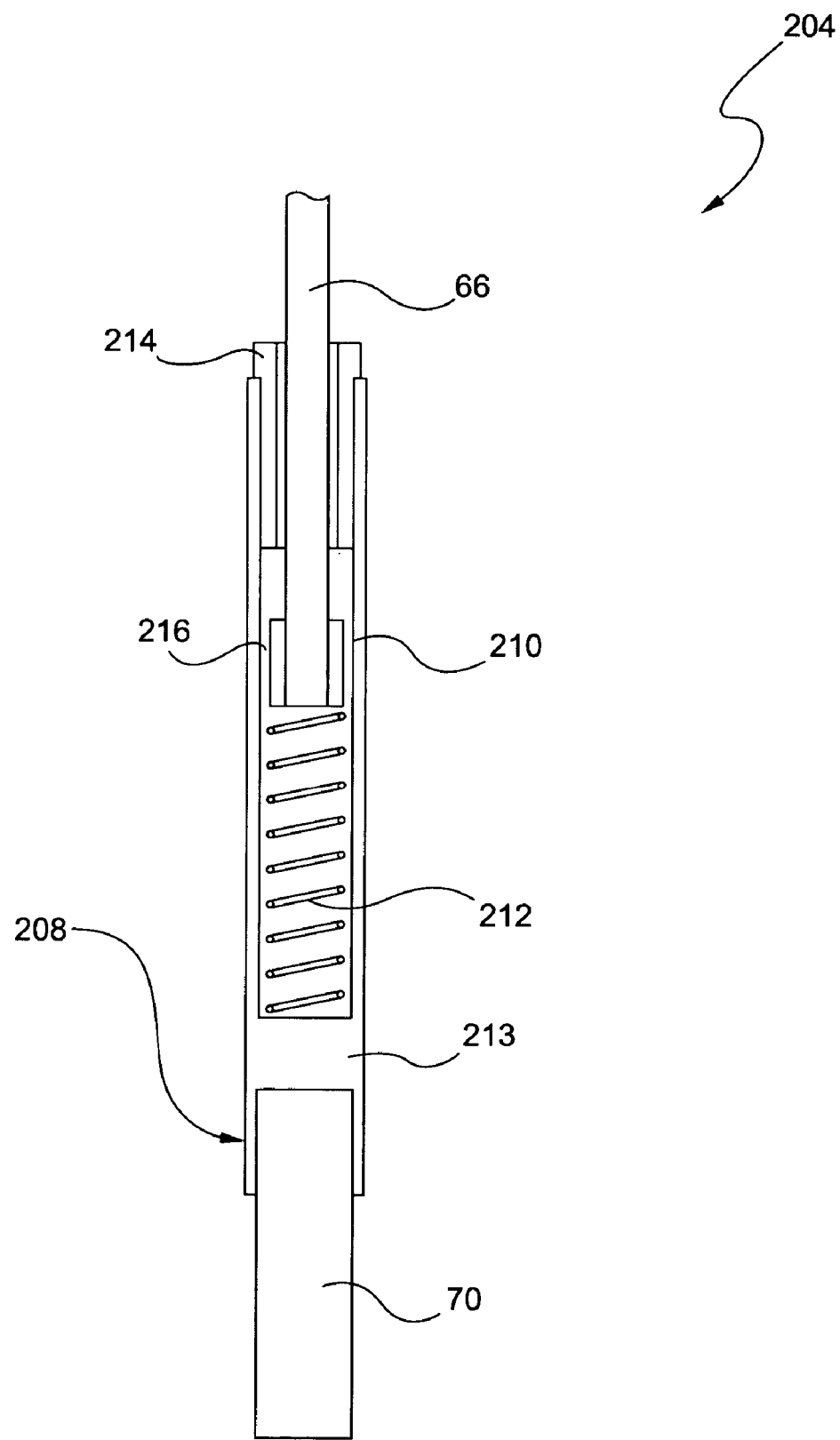
FIG. 22 is a cross-sectional view of the magnet, compensating device and magnet rod shown in FIGS. 20 and 21.

Turning now to FIGS. 20-22, a preferred embodiment of the primary magnet unit 18 is shown in further detail. As discussed above, the primary magnet unit 18 includes an array of pins 47 supported in a head assembly 38. Each pin 47 includes a hollow pin body 45 having one end secured within a respective bore 202 formed in the head assembly 38. Removably attached to the opposite end of the hollow pin body 45 is a disposable tip 84. An actuating element 70, which, in this embodiment, is a permanent magnet, is movably disposed within the hollow pin body 45 between an "up" position, as shown in FIG. 20, to a "down" position, as shown in FIG. 21. In its down position, the magnet 70 is positioned at the end of the disposable tip 84 to apply a magnetic force through the tip. When the magnet 70 is moved to its up position, as shown in FIG. 20, the magnetic force applied by the magnet is removed from the tip.

The magnet 70 is driven between its up and down position by the magnet actuator system 40, as described above. In particular, selective activation of individual electromagnets 61 causes the selected electromagnet to magnetically engage a respective ferromagnetic piston 65 fixed to an end of an actuator rod 66, also termed a magnet rod. As the actuator plate 60 moves the electromagnets 61 downward, all of the magnetically engaged pistons 65 and associated actuator rods 66 are also brought downward, whereby selected magnets 70 are moved into their down position.

In a preferred embodiment, each magnet rod 66 is connected to a respective magnet 70 via a compensating device 204. In general, the compensating device 204 compensates for any variations in the stroke length of the magnet rod 66 so that intimate contact between the magnet 70 and the bottom wall 206 of the disposable tip 84 is maintained when the magnet is in its down position. More specifically, as the magnet actuator system 40 drives the magnet rod 66 downward, as shown in FIG. 21, the compensating device 204 will transfer the downward force from the magnet rod to the magnet 70 to move the magnet into its down position, wherein the magnet comes into contact with the bottom 206 of the disposable tip 84. Once the magnet 70 makes contact with the bottom 206 of the tip 84, any further downward movement of the magnet rod 66 will be absorbed by the compensating device 204 so that the magnet will not break through the tip bottom.

The compensating device 204 can take various forms. In simplest terms, the compensating device 204 is preferably a resilient element which urges or biases the magnet 70 against the bottom 206 of the disposable tip 84 and can absorb downward motion of the magnet rod 66 so that the magnet does not break through the tip bottom. In this regard, the compensating device 204 can simply consist of a solid resilient cushioning material, for example, disposed between the magnet 70 and the magnet rod 66.

However, in a preferred embodiment, the compensating device 204 includes a tubular member 208 having a central bore 210 and a spring 212 disposed within the central bore, as shown in FIG. 22. The tubular member 208 can be open ended, or the central bore 210 can be separated into two portions by an integral wall 213, as shown in FIG. 22. The magnet 70 is fixed to one end of the tubular member 208 and the magnet rod 66 is movably attached at the opposite end of the tubular member so that the end of the magnet rod engages the spring 212 disposed within the bore 210 of the tubular member. To facilitate attachment of the magnet rod 66 to the compensating device 204, the tubular member 208 can include a bushing 214 fixed at an open end thereof, opposite the magnet 70, for slidably receiving the outer surface of the magnet rod. Also, the magnet rod 66 can include a shoulder 216 disposed at its end, which is captured within the central bore 210 of the tubular member by the bushing 214. The shoulder 216 preferably has a size enabling it to compress the spring 212 upon downward movement of the magnet rod 66. In this embodiment, the compensating device 204 is a self-contained unit, which is easily extracted, should it have to be replaced or cleaned, and interchangeable with other magnet rods 66.

In use, when the magnet 70 reaches the bottom 206 of the tip 84, any further downward motion of the magnet rod 66 will depress the spring 212 disposed within the central bore 210 of the tubular member 208. In this regard, the spring 212 is preferably sized to exert a force on the bottom 206 of the tip 84 which is less than the force required to remove the tip from the pin body 45. For example, if it is found that the pressure required to remove the plastic tip 84 from the hollow pin body 45 is at least 400 to 500 grams, a suitable spring 212 exerting a pressure of about 50 grams should be selected for use in the compensating device 204 of the present invention. As a result, the spring 212 will allow the magnet 70 to be completely pressed (and remain in place) against the bottom 206 of the tip 84, but not beyond.

It has been found that such intimate contact between the magnet 70 and the bottom 206 of the tip 84 provides the greatest efficiency in magnetic particle attraction. The thickness of the bottom 206 of the tip 84 is preferably about 30 microns and any gap between the magnet 70 and the bottom of the tip will proportionately increase the distance between the magnet and the magnetic particles, resulting in a decrease of efficiency in magnetic particle attraction.

Figure 23:
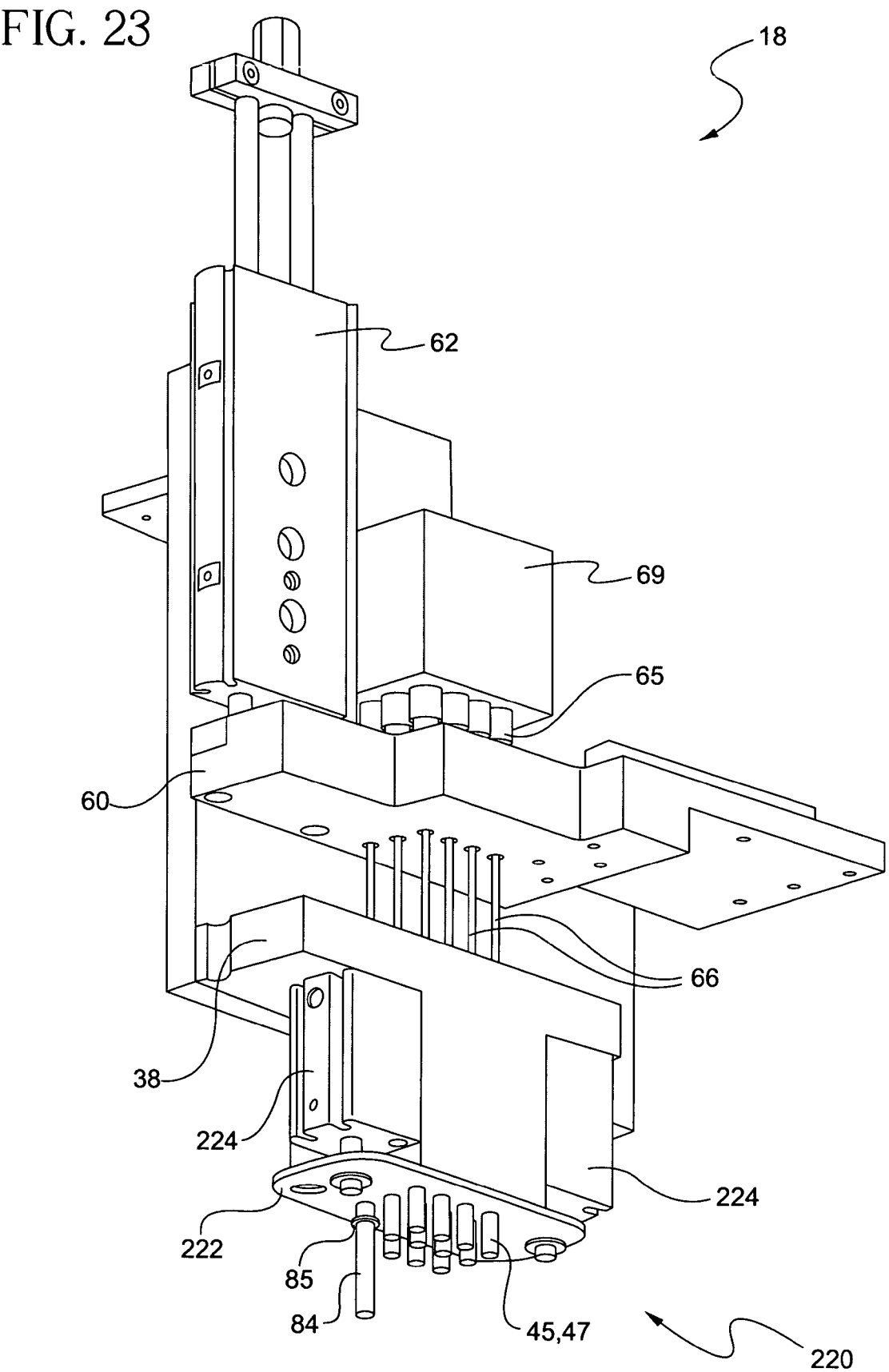
FIG. 23 is a perspective view of the primary transfer unit showing a preferred embodiment of a tip ejector.

Also shown in FIGS. 20-21, and additionally in FIG. 23, is an alternative embodiment of a tip ejector 220. Thus, instead of providing a separate tip insertion/removal station 22, as described above, a tip ejector 220 can be provided directly on the head assembly 38 of the primary magnet unit 18. The tip ejector 220 preferably includes an ejector plate 222 and at least one pneumatic drive 224 secured to the head assembly 38 for moving the ejector plate toward and away from the head assembly. The ejector plate 222 has a plurality of holes or apertures 226 matching in number and arrangement with the pins 47. Each hole 226 has a diameter slightly larger than the diameter of the pin body 45, but is slightly smaller than the diameter of the upper rim 85 of the disposable tip 84. The ejector plate 222 is preferably connected on opposite sides with two pneumatic cylinder drives 224 fixed to the head assembly. The ejector plate 222 is positioned so that each of the holes 226 has a respective pin 47 received therein.

In use, the ejector plate 222 is kept in an upward position toward the head assembly 38 during operation of the primary magnet unit 18. Once sample transfer operations are complete, the pneumatic drives 224 are activated to move the ejector plate 222 downward away from the head assembly 38. Since the holes 226 in the ejector plate are smaller than the dimension of the tip rim 85, as the ejector plate moves downward, the edges of the plate surrounding the holes will make contact with the rims of the tips and force the tips downward off the pin bodies 45. As described above, a tip receptacle 98 can be provided to catch the disposed tips 84 removed from the pin bodies 45 by the ejector 220.

Figure 24:
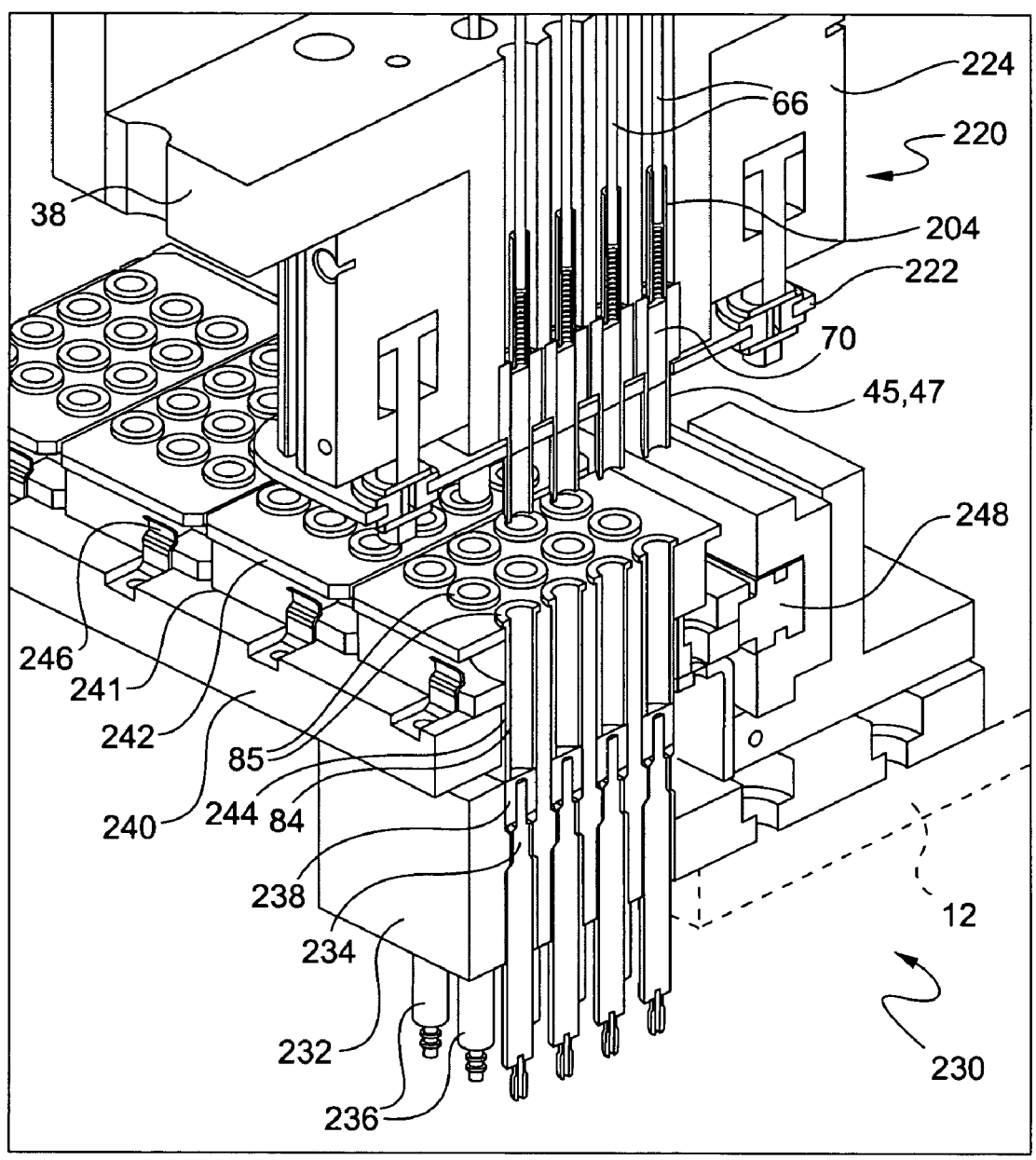
FIG. 24 is a perspective view of a preferred embodiment of a tip loading station.
Figure 25:
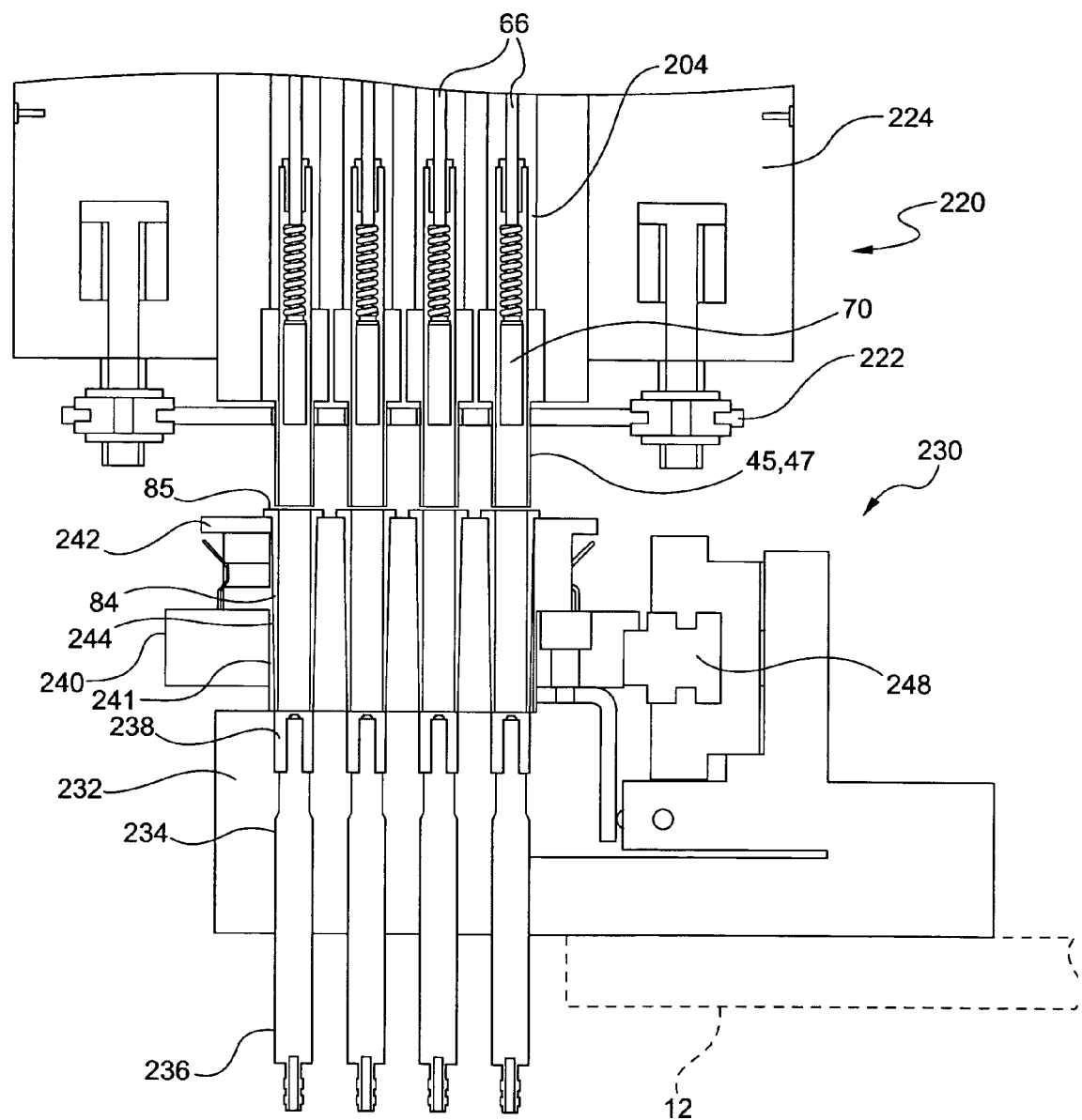
FIG. 25 is a cross-sectional view of the tip loading station shown in FIG. 24.

FIGS. 24 and 25 additionally show an alternative embodiment of a tip loading station 230. The tip loading station 230 is generally similar to the tip insertion unit 79, described above, for applying the disposable tips 84 to the ends of the pins 47 of the multi-pin array 46. Thus, like the tip insertion unit 79, the tip loading station 230 includes a base 232 fixed to the system frame 12 and having an array of cylindrical bores 234 formed therethrough. The spacing and arrangement of the bores 234 coincides with the spacing and arrangement of the pins 47 supported on the head assembly 38 of the primary magnet unit 18. Thus, in the drawings a 4×3 array of twelve cylindrical bores 234, matching the spacing and arrangement of the pins 47, is provided in the base 232.

Connected to each cylindrical bore 234 is an air supply connector 236, which is connected to an air supply source (not shown) for supplying a positive air pressure to the cylindrical bore. Furthermore, a tip loading piston 238 is slidably disposed within each cylindrical bore 234 to force the tips 84 onto their respective pins 47 during tip insertion, as will be described in further detail below. As discussed above, selection of the tips to be loaded can be made via the central control unit 24 or a tip selection control pad 92 provided separate from the central control unit.

Disposed above the base 232 is a sub-base 240, which supports at least one tip cassette 242. The sub-base 240 preferably includes a cassette pocket 241 formed through the sub-base for receiving the tip cassette 242. Thus, the pocket 241 positively positions the tip cassette 242 with respect to the sub-base 240. Preferably, the sub-base 240 includes a continuous pocket 241 or a plurality of pockets to positively position a plurality of tip cassettes 242. FIG. 24 shows four tip cassettes 242 removably retained and positively positioned on top of the sub-base 240 by way of retaining clips 246. It is conceivable that other structure can be utilized to position and retain the tip cassettes.

The sub-base 240 is preferably linearly translatable with respect to the tip insertion base 232 to accurately position each tip cassette 242 over the piston bores 234 formed in the base. The sub-base 240 can be made translatable with respect to the base 232 via a cooperating rail structure 248. The sub-base 240 can slide manually along the rail 248, or a drive unit (not shown) can be provided to move the sub-base. In either case, the sub-base 240 and/or base 232 is preferably provided with indexing stops 250 to positively position the sub-base 240 with respect to the base 232. For example, if four tip cassettes 242 are positioned on the sub-base 240, the sub-base and/or the base 232 will include four indexing stops 250 to positively position each cassette over the array of cylindrical bores 234 in the base 232. Such stops 250 can simply consist of alignment holes formed in the sub-base 240 and base 232, as shown in FIG. 25. A pin (not shown), for example, can also be inserted in the alignment holes to hold the sub-base in position.

Formed through the tip cassette 242 is an array of holes 244, which are sized to respectively receive a disposable protective tip 84, with the rim 85 of the tip resting on the upper surface of the cassette. The spacing and arrangement of the holes 244 in the tip cassette 242 coincides with the spacing and arrangement of the pins 47 supported on the head assembly 38 and the spacing and arrangement of the cylindrical piston bores 234 of the tip insertion base 232. Again, the drawings show a preferred 4×3 array.

Operation of the tip loading station 230 is similar to that described above. In particular, once a loaded cassette 242 has been positioned above the piston bores 234 of the base 232, the head assembly 38 of the primary magnet unit 18 is positioned above the tip cassette by the y and z stepper motors 42 and 44 and then gently brought down in the z-direction until the ends of the pin bodies 45 are in close proximity to the disposable tips 84. The tips 84 to be loaded can then be entered in the control unit 24, whereby a burst of air pressure supplied through the respective air supply connector 236 will drive the selected tip loading pistons 238 upwardly into the bores 244 of the tip cassette 242 to force the tips 84 upwardly out of the cassette to frictionally engage the pin bodies 45. Release of the air pressure will return the pistons 238 down into the base 232, whereby the sub-base 240 can be translated to move another tip cassette 242 over the piston bores 234 to repeat the process.

Figure 26:
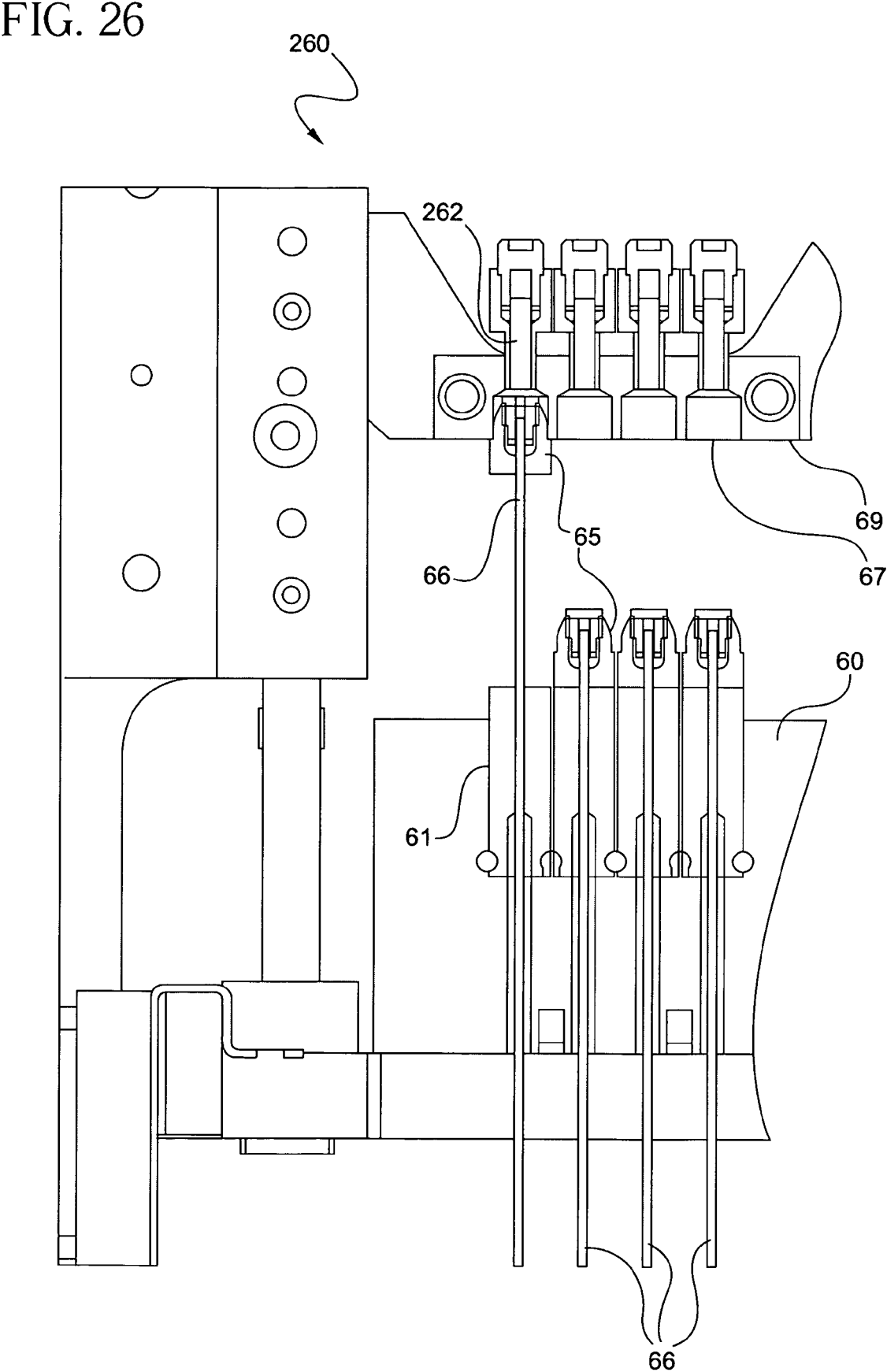
FIG. 26 is a cross-sectional view of an alternative embodiment of the magnet actuator system of the present invention.

FIG. 26 shows an alternative embodiment of a magnet actuator system 260, wherein the tension springs 71 provided in the bores 67 of the piston housing 69 for biasing the magnet rods 66 in an upward position have been replaced by permanent magnets 262. In particular, a permanent magnet 262 is fixed within each bore 67 of the piston housing 69 to magnetically attract the ferromagnetic piston 65 fixed at the end of the magnet rod 66.

When not magnetically engaged with a solenoid electromagnet 61, the ferromagnetic piston 65 will be magnetically retained by the permanent magnet 262 in an upward position within its respective bore 67 of the piston housing 69, as illustrated by the left-most piston 65 shown in FIG. 26. However, upon activation, the solenoid electromagnet 61 will counteract the magnetic force applied by the permanent magnet 262 and will pull the piston 65 away from the permanent magnet when moved into proximity with the piston. Activated electromagnets 61 pulling pistons 65 away from the permanent magnets 262 are illustrated by the three electromagnets on the right side of FIG. 26.

It has been found that the initial force needed to disconnect the piston 65 from the permanent magnet 262 can be achieved by applying a voltage of about 12-15V to the electromagnet 61. Once the piston 65 has been pulled free from the permanent magnet 262, this force can be drastically reduced, wherein application of only 6V to the electromagnet 61 is required. Such reduction of voltage applied to the electromagnet 61 results in a reduction of heat produced by the solenoid electromagnet and reduces the wear on the electromagnet.

Figure 27:
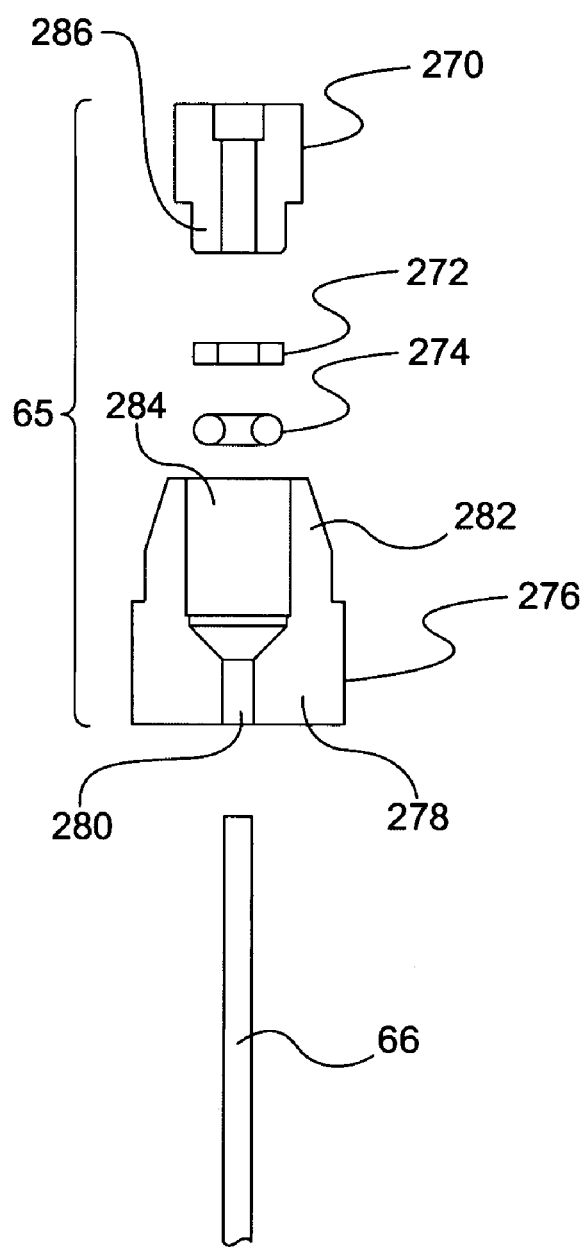
FIG. 27 is an exploded cross-sectional view of the end of the magnet rod shown in FIG. 26.

Also shown in FIG. 26, and in additional detail in FIG. 27, is the connection between the magnet rod 66 and the ferromagnetic piston 65 according to a preferred embodiment of the present invention. In particular, the ferromagnetic piston 65 preferably includes a magnet retractor 270, a washer 272, an O-ring 274 and a cone fitting 276. The magnet retractor 270 and the cone fitting 276 are made from a ferromagnetic material to be respectively attracted by the permanent magnet 262 and the solenoid electromagnet 61.

The cone 276 includes a proximal end 278 having an aperture 280 formed therein for receiving the end of the magnet rod 66. The distal end 282 of the cone 276 opposite the proximal end 278 is preferably conical in shape to facilitate seating of the piston 65 within its respective piston bore 67 of the piston housing 69. The distal end 282 further includes a bore 284 communicating with the magnet rod aperture 280. The distal end bore 284 is sized to receive the O-ring 274, the washer 272 and a proximal end 286 of the magnet retractor 270. In this regard, the outer surface of the proximal end 286 of the magnet retractor 270 and the inner surface of the cone bore 284 are preferably provided with mating threads so that the retractor and the cone 276 can be threadably engaged to form the piston 65.

Upon assembly, the magnet rod 66 is slipped through the aperture 280 formed in the proximal end 278 of the cone 276. The O-ring 274 has an inner diameter matching the outer diameter of the magnet rod 66 and is slipped over the end of the rod extending into the cone. The washer 272 is placed on top of the O-ring 274 and the magnet retractor 270 is threaded into the bore 284 to compress the O-ring. As the O-ring 274 is compressed, it expands radially inward to grip the outer surface of the magnet rod 66. Such gripping force is sufficient to firmly retain the rod 66 to the piston 65.

As a result of the present invention, a three axis transfer device control system is provided which enables the separation and transfer of any desired combination of samples with the advantage of executing multiple tests in a single run. The design offers significant advantages in addition to the accuracy of movement, reliability, reduction in cost of the process and efficiency. The flexibility of the system due to the several modes of operation (combinatorial functionality) allows the system to be operated as a fixed transfer device with the capability of breaking the array into smaller sub-arrays.

The system according to the present invention is ideally suited for a variety of analytical applications involving samples, such as DNA, proteins, peptides, hormones etc. The system according to the present invention is further well adapted to conduct false positive testing of samples, which is an essential step performed in all medical labs. In such a procedure, the system of the present invention will capture expensive magnetic reagents in those wells that had negative test results and, after washing with a fresh washing liquid, the magnetic reagents will then be ready for another set of samples instead of being discarded.

Such a procedure can be conducted as follows. First, all wells that show a binding surface reaction to the magnetic particles and the target gene (i.e., a positive result) are located. It should be noted that the non-reactive particles in the non-positive wells could now be captured and washed, or the process can proceed later after the below procedures are completed.

Next, the controller of the present invention is activated to engage the pin units on the "positive" reacted wells. The pin units that are engaged will capture the magnetic particles in the "positive" wells and move the positive particles to new wells, which contain a washing liquid. Preferably, these positive colored particles are divided into two groups, so that half is in one well and the other half is in a second well. As a result, a control well and a test well are established.

The control well is left alone and the "test" well's particles are washed according to the combinatorial washing process described above. The washing will determine whether there is a "real" positive or a "false" positive. In particular, if the binding stays intact, it is a real positive and if the washing strips off the non-specific bound colored reagent, it is a "false" positive.

To determine the color level in both the control and the newly washed test, a camera or visual inspection can be utilized. With camera inspection, a computer system can be implemented to compare the initial color level of the control with the washed tests. If there is a difference in the color, there is a "false" positive. To insure that the "false" positive is truly a false result, the process is repeated with fresh new particles and with a fresh small amount from the original sample(s) that gave the false positive.

For example, with a ninety-six well plate, if four wells were determined to be positive and ninety-two were negative (i.e., the magnetic particles did not react with the samples in ninety-two wells), the pins for these ninety-two wells are selected to carry out magnetic separation in these wells. This will constitute the first cleaning and washing. Then, an extensive washing sequence can be carried out, wherein each wash is done with a fresh washing liquid. This will effectively eliminate any contaminants from these wells.

While the system of the present invention has been primarily described herein as a system utilizing magnetic forces for attracting and releasing magnetic particles, those skilled in the art will appreciate that the three axis coordinate control system of the present invention may also be employed to control movement of an array of pipettes or other transferring devices to transfer samples from one or more source vessels to one or more target vessels using known techniques. Such a device is intended to come within the scope of the invention. In particular, as mentioned herein, the system may simply include a vessel drive unit including a translatable support plate for supporting the source vessel and the target vessel thereon and a support plate drive for reciprocally translating the support plate in an x-direction. Also, in this case, the primary magnet unit would simply be termed a primary transfer unit and would include at least one transfer device.

Although the preferred embodiments of the present invention have been described with reference to the accompanying drawing, it is to be understood that the invention is not limited to those precise embodiments, and that other changes and modifications may be made by one skilled in the art without departing from the scope or spirit of the invention.

What is claimed is:

1. A transfer device for transferring a sample from a source vessel to a target vessel, the transfer device comprising:
   a pin tip having a central bore terminating at a bottom wall;
   an actuating element movably disposed in said pin tip bore between a first position adjacent said pin tip bottom wall and a second position away from said bottom wall, said movement of said actuating element causing a sample in proximity to said pin tip to be alternately collected and released from said pin tip;
   an actuator rod for moving said actuating element between said first and second positions, said actuator rod defining a stroke length associated with said movement, and wherein said actuator rod is linearly translatable relative to said actuating element; and
a compensating device connected between said actuating element and said actuator rod for compensating for any variations in said actuator rod stroke length with respect to said actuating element,
wherein said compensating device urges said actuating element into contact with said pin tip bottom wall at said first position, and
wherein said compensating device comprises a resilient element for biasing said actuating element against said pin tip bottom wall at said first position.

2. A transfer device as defined in claim 1, wherein said actuating element is a magnet, and wherein a magnetic force is applied at said pin tip bottom wall when said magnet is at said first position and said magnetic force is removed from said pin tip bottom wall when said magnet is moved to said second position.

3. A transfer device as defined in claim 1, wherein said compensating device comprises a tubular member having a central bore and a spring disposed within said bore, said actuating element being fixed at one end of said tubular member and said actuator rod movably extending into said central bore to engage said spring.

4. A transfer unit for transferring a sample from a source vessel to a target vessel, the transfer unit comprising:
a head assembly;
a transfer device supported on said head assembly, said transfer device having a tip removably attached to an end thereof, said tip having a central bore terminating at a bottom wall;
a tip ejector supported on said head assembly for removing said tip from said transfer device;
an actuating element movably disposed in said tip bore between a first position adjacent said tip bottom wall and a second position away from said bottom wall, said movement of said actuating element causing a sample in proximity to said tip to be alternately collected and released from said tip;
an actuator rod for moving said actuating element between said first and second positions, said actuator rod defining a stroke length associated with said movement; and
a compensating device connected between said actuating element and said actuator rod for compensating for any variations in said actuator rod stroke length, said compensating device urging said actuating element into contact with said tip bottom wall at said first position and including a tubular member having a central bore and a spring disposed within said bore, said actuating element being fixed at one end of said tubular member and said actuator rod movably extending into said central bore to engage said spring.

5. A transfer unit as defined in claim 4,
wherein said tip ejector comprises:
an ejector plate having an aperture defined by an edge, said transfer device extending through said aperture; and
a drive supported on said head assembly and connected to said ejector plate for moving said ejector plate away from said head assembly, wherein said aperture edge engages said tip attached to said transfer device to remove said tip from said transfer device upon movement of said ejector plate away from said head assembly.

6. A transfer unit as defined in claim 4, further comprising:
a supporting frame movably supporting said head assembly; and
a tip loading station supported on said frame for loading said tip onto said transfer device.

7. A transfer unit for transferring a sample from a source vessel to a target vessel, the transfer unit comprising:
a head assembly;
a transfer device supported on said head assembly, said transfer device having a tip removably attached to an end thereof;
a tip ejector supported on said head assembly for removing said tip from said transfer device;
a supporting frame movably supporting said head assembly; and
a tip loading station supported on said frame for loading said tip onto said transfer device, wherein said tip loading station comprises:
a base having a bore formed therein, said bore having a proximal end terminating at an upper surface of said base and a distal end;
a sub-base supported on said upper surface of said base, said sub-base supporting said tip for application to said transfer device; and
a pressure source connected to said distal end of said base bore for applying a pressure through said base bore for forcing said tip from said sub-base onto said transfer device.

8. A transfer unit as defined in claim 7, wherein said tip of said transfer device has a central bore terminating at a bottom wall and said transfer device further comprises:
an actuating element movably disposed in said tip bore between a first position adjacent said tip bottom wall and a second position away from said bottom wall, said movement of said actuating element causing a sample in proximity to said tip to be alternately collected and released from said tip;
an actuator rod for moving said actuating element between said first and second positions, said actuator rod defining a stroke length associated with said movement; and
a compensating device connected between said actuating element and said actuator rod for compensating for any variations in said actuator rod stroke length.

9. A transfer unit as defined in claim 8, wherein said actuating element is a magnet, and wherein a magnetic force is applied at said tip bottom wall when said magnet is at said first position and said magnetic force is removed from said tip bottom wall when said magnet is moved to said second position.

10. A transfer unit as defined in claim 8, wherein said compensating device urges said actuating element into contact with said tip bottom wall at said first position.

11. A transfer unit as defined in claim 10, wherein said compensating device comprises a resilient element for biasing said actuating element against said tip bottom wall at said first position.

12. A transfer unit as defined in claim 7, wherein said base further includes a piston slidably received within said base bore, said piston being driven by said pressure applied by said pressure source to force said tip from said sub-base onto said transfer device.

13. A transfer unit as defined in claim 7, wherein said sub-base is adapted to support a plurality of tips and is translatable with respect to said base to positively position said tips over said base bore.

14. A transfer unit as defined in claim 7, wherein said tip loading station further comprises a tip cassette supported on said sub-base, said tip cassette having a bore formed therethrough, said bore being sized to receive said tip and having a distal end terminating at said upper surface of said base.

15. An apparatus for transferring a sample from a source vessel to a target vessel comprising:
- a transfer unit including a transfer device for transferring a sample;
- a supporting frame movably supporting said transfer unit; and
- a tip loading station supported on said supporting frame for loading a tip onto an end of said transfer device, wherein said tip loading station comprises:
  - a base having a bore formed therein, said bore having a proximal end terminating at an upper surface of said base and a distal end;
  - a sub-base supported on said upper surface of said base, said sub-base supporting said tip for application to said transfer device; and
  - a pressure source connected to said distal end of said base bore for applying a pressure through said base bore for forcing said tip from said sub-base onto said transfer device.

16. An apparatus as defined in claim 15, wherein said base further includes a piston slidably received within said base bore, said piston being driven by said pressure applied by said pressure source to force said tip from said sub-base onto said transfer device.

17. An apparatus as defined in claim 15, wherein said sub-base is adapted to support a plurality of tips and is translatable with respect to said base to positively position said tips over said base bore.

18. An apparatus as defined in claim 15, wherein said tip loading station further comprises a tip cassette supported on said sub-base, said tip cassette having a bore formed therethrough, said bore being sized to receive said tip and having a distal end terminating at said upper surface of said base.

19. A transfer unit for transferring a sample from a source vessel to a target vessel comprising:
- a transfer device having a hollow body and an actuating element movably disposed in said hollow body between a first and a second position, said movement of said actuating element causing a sample in proximity to said transfer device to be alternately collected and released from said transfer device;
- an actuator plate having at least one individually activated electromagnet disposed thereon;
- an actuator plate drive for reciprocally translating said actuator plate;
- an actuator rod having a first end and a second end, said first end connected to said actuating element in said hollow body of said transfer device;
- a ferromagnetic piston disposed on said second end of said actuator rod, said piston being engageable with said electromagnet when said electromagnet is activated for moving said actuating element from said first position to said second position upon translation of said actuator plate; and
- a piston housing spaced from said actuator plate, said piston housing including a magnet for biasing said piston toward said piston housing.

20. A transfer unit as defined in claim 19, wherein said actuating element of said transfer device is a magnet slidably disposed within said hollow body between said first position adjacent a tip of said transfer device, wherein a magnetic force is applied at said tip, and said second position away from said tip, wherein said magnetic force is removed from said tip for alternately collecting and releasing samples from said transfer device.

21. A transfer unit as defined in claim 19, wherein said piston comprises:
- a ferromagnetic cone fitting having an aperture formed in a proximal end thereof for receiving said second end of said actuator rod and a bore formed in a distal end thereof;
- an O-ring disposed in said cone fitting bore around said second end of said actuator rod; and
- a ferromagnetic retractor fitted in said cone fitting bore for compressing said O-ring into gripping engagement with said actuator rod.

* * * * *

UNITED STATES PATENT AND TRADEMARK OFFICE
CERTIFICATE OF CORRECTION

PATENT NO. : 7,597,520 B2
APPLICATION NO. : 11/311558
DATED : October 6, 2009
INVENTOR(S) : Zobel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 875 days.

Signed and Sealed this

Twenty-eighth Day of September, 2010

David J. Kappos
*Director of the United States Patent and Trademark Office*